United States Patent
Fuchs et al.

(10) Patent No.: US 9,504,760 B2
(45) Date of Patent: Nov. 29, 2016

(54) IMMUNOMODULATING NANOPARTICULATE COMPOSITION

(76) Inventors: Sebastian Fuchs, Munich (DE);
Conrad Coester, Neuhof (DE);
Heidrun Gehlen, Berlin (DE); John Klier, Grosskarolinenfled (DE);
Gerhard Winter, Penzberg (DE)

( * ) Notice: Subject to any disclaimer, the term of this patent is extended or adjusted under 35 U.S.C. 154(b) by 0 days.

(21) Appl. No.: 13/413,377

(22) Filed: Mar. 6, 2012

(65) Prior Publication Data

US 2012/0231041 A1 Sep. 13, 2012

(30) Foreign Application Priority Data

Mar. 7, 2011 (EP) .................................... 11001858

(51) Int. Cl.
*A61K 39/00* (2006.01)
*A61K 9/72* (2006.01)
*B82Y 5/00* (2011.01)
*A61K 47/48* (2006.01)
*A61K 9/00* (2006.01)

(52) U.S. Cl.
CPC ....... *A61K 47/48884* (2013.01); *A61K 9/0078* (2013.01)

(58) Field of Classification Search
CPC ..................... A61K 39/39; A61K 2039/5258; A61K 2039/55555; A61K 2039/55561; A61K 39/12; A61K 47/48776; A61K 47/48892; A61K 49/0004; A61K 49/0093; A61K 49/0097; A61K 47/48884; A61K 9/0024; A61K 9/0078
USPC .......... 424/184.1, 193.1, 278.1, 400
See application file for complete search history.

(56) References Cited

U.S. PATENT DOCUMENTS

2012/0171229 A1* 7/2012 Zepp et al. ................ 424/184.1

FOREIGN PATENT DOCUMENTS

WO WO 2007068747 A1 * 6/2007

OTHER PUBLICATIONS

Brzoska et al. Biochem Biophys Res Commun. May 28, 2004;318(2):562-70.*
Fonseca D E et al: "Use of CpG oligonucleotides in treatment of asthma and allergic disease", Advanced Drug Delivery Reviews, Elsevier BV, Amsterdam, NL, vol. 61, No. 3, Mar. 28, 2009, pp. 256-262.*
Klaus Zwiorek et al: "Delivery by Cationic Gelatin Nanoparticles Strongly Increases the Immunostimulatory Effects of CpG Oligonucleotides", Pharmaceutical Research, Kluwer Academic Publishers—Plenum Publishers, NL, vol. 25, No. 3, Oct. 3, 2007, pp. 551-562.*
Kerkmann et al. J. Biol Chem. Mar. 4, 2005;280(9)8086-93.*

* cited by examiner

*Primary Examiner* — Janet Epps-Smith

(57) ABSTRACT

The present invention relates to a preferably nebulizable pharmaceutical composition comprising a pharmaceutically acceptable protein-based nanocarrier preferably in the size range 150 to 300 nm and a preventative or therapeutic amount of an active agent for use in the prevention and/or treatment of an allergic and/or inflammatory disease of the lower airways in a mammal. Preferably, the active agent is a CpG oligodeoxynucleotide (CpG-ODN), and preferably the composition exhibits a prolonged clinical effect.

15 Claims, 4 Drawing Sheets ium bromide provide addition benefit when used in combination with SABA in

SEQUENCE LISTING

<160> NUMBER OF SEQ ID NOS: 14

<210> SEQ ID NO 1
<211> LENGTH: 24
<212> TYPE: DNA
<213> ORGANISM: Artificial
<220> FEATURE:
<223> OTHER INFORMATION: artificially synthetized oligodeoxynucleotide

<400> SEQUENCE: 1
ctggtctttc tggttttttt ctgg                                          24

<210> SEQ ID NO 2
<211> LENGTH: 20
<212> TYPE: DNA
<213> ORGANISM: Artificial
<220> FEATURE:
<223> OTHER INFORMATION: artificially synthetized oligodeoxynucleotide

<400> SEQUENCE: 2
gggggacgat cgtcggggggg                                              20

<210> SEQ ID NO 3
<211> LENGTH: 27
<212> TYPE: DNA
<213> ORGANISM: Artificial
<220> FEATURE:
<223> OTHER INFORMATION: artificially synthetized oligodeoxynucleotide

<400> SEQUENCE: 3
tcgcgtgcgt tttgtcgttt tgacgtt                                       27

<210> SEQ ID NO 4
<211> LENGTH: 24
<212> TYPE: DNA
<213> ORGANISM: Artificial
<220> FEATURE:
<223> OTHER INFORMATION: artificially synthetized oligodeoxynucleotide

<400> SEQUENCE: 4
tcgtcgtttt gtcgttttgt cgtt                                          24

<210> SEQ ID NO 5
<211> LENGTH: 21
<212> TYPE: DNA
<213> ORGANISM: Artificial
<220> FEATURE:
<223> OTHER INFORMATION: Artificially synthetized oligodeoxynucleotide

<400> SEQUENCE: 5
tcgtcgtttt cggcgcgcgc c                                             21

<210> SEQ ID NO 6
<211> LENGTH: 25
<212> TYPE: DNA
<213> ORGANISM: Artificial
<220> FEATURE:
<223> OTHER INFORMATION: artificially synthetized oligodeoxynucleotide

<400> SEQUENCE: 6
tcgtcgtcgt tcgaacgacg ttgat                                         25

<210> SEQ ID NO 7
<211> LENGTH: 20
<212> TYPE: DNA
<213> ORGANISM: Artificial

```
<220> FEATURE:
<223> OTHER INFORMATION: artificially synthetized oligodeoxynucleotide

<400> SEQUENCE: 7
ggtgcatcga tgcagggggg                                              20

<210> SEQ ID NO 8
<211> LENGTH: 22
<212> TYPE: DNA
<213> ORGANISM: Artificial
<220> FEATURE:
<223> OTHER INFORMATION: Artificially synthetized oligodeoxynucleotide

<400> SEQUENCE: 8 ggggggggacg atcgtcgggg gg                                          22

<210> SEQ ID NO 9
<211> LENGTH: 24
<212> TYPE: DNA
<213> ORGANISM: Artificial
<220> FEATURE:
<223> OTHER INFORMATION: Artificially synthetized oligodeoxynucleotide

<400> SEQUENCE: 9 gggggggggac gatcgtcggg gggg                                        24

<210> SEQ ID NO 10
<211> LENGTH: 26
<212> TYPE: DNA
<213> ORGANISM: Artificial
<220> FEATURE:
<223> OTHER INFORMATION: Artificially synthetized oligodeoxynucleotide

<400> SEQUENCE: 10
ggggggggga cgatcgtcgg gggggg                                       26

<210> SEQ ID NO 11
<211> LENGTH: 26
<212> TYPE: DNA
<213> ORGANISM: Artificial
<220> FEATURE:
<223> OTHER INFORMATION: Artificially synthetized oligodeoxynucleotide

<400> SEQUENCE: 11
gggggggggg acgatcgtcg gggggg                                       26

<210> SEQ ID NO 12
<211> LENGTH: 30
<212> TYPE: DNA
<213> ORGANISM: Artificial
<220> FEATURE:
<223> OTHER INFORMATION: Artificially synthetized oligodeoxynucleotide

<400> SEQUENCE: 12
gggggggggg gacgatcgtc gggggggggg                                   30

<210> SEQ ID NO 13
<211> LENGTH: 32
<212> TYPE: DNA
<213> ORGANISM: Artificial
<220> FEATURE:
<223> OTHER INFORMATION: Artificially synthetized oligodeoxynucleotide

<400> SEQUENCE: 13
gggggggggg ggacgatcgt cgggggggggg gg                               32
```

-continued

```
<210> SEQ ID NO 14
<211> LENGTH: 34
<212> TYPE: DNA
<213> ORGANISM: Artificial
<220> FEATURE:
<223> OTHER INFORMATION: Artificially synthetized oligodesoxynucleotide

<400> SEQUENCE: 14
gggggggggg gggacgatcg tcgggggggg gggg                                   34
```

IMMUNOMODULATING NANOPARTICULATE COMPOSITION This application takes benefit of the foreign priority of application EP 11001858 filed on Mar. 7, 2011.

TECHNICAL FIELD

The present invention relates to a pharmaceutical composition comprising a pharmaceutically acceptable polymerized protein-based nanocarrier preferably in the size range 150 to 300 nm and a preventative or therapeutic amount of an active agent for use in the prevention and/or treatment of an allergic and/or inflammatory disease of the lower airways in a mammal. Preferably, the active agent is an oligonucleotide and/or an oligodeoxynucleotide (ODN) which is effective for use in the prevention and/or treatment of an allergic and/or inflammatory disease of the lower airways, which is preferably selected from the group consisting of guanidine phosphodiester cytosine (CpG) ODN class A, class B and/or class C. Said pharmaceutical composition preferably has a prolonged effect in the prevention and/or treatment of an allergic and/or inflammatory disease of the lower airways, preferably at a surprisingly low dose.

The allergic or inflammatory disease is preferably associated with elevated serum and/or pulmonary interleukin (IL-10) levels, and to methods for the production of said composition for use in the prevention and/or treatment of allergic and/or inflammatory diseases of the lower airways.

BACKGROUND OF THE INVENTION

The overwhelming necessity for effective and causal treatment of allergic diseases is well known in the art. Within the large group of allergic diseases, which are in general characterized by versatile hypersensitivity type I reactions caused by a disordered activation of the immune system and which comprise allergic rhinitis, asthma bronchiale, atopic eczema, anaphylaxis, insect venom, drug allergies, food allergies and multiple allergies, allergic airway diseases such as asthma are among the most prevalent ones to impair quality of life and life expectation. In the last decades, allergic airway diseases have dramatically increased in the northern hemisphere of industrialized countries humans and domestic animals such as horses (Kline 2007; Braun-Fähränder 2009). As of 2009, 300 million people worldwide were affected by asthma leading to approximately 250,000 deaths per year. It is estimated that asthma has a 7-10% prevalence worldwide with a great disparity in prevalence worldwide across the world (as high as a 20 to 60-fold difference). A trend toward more developed and westernized countries having higher rates of asthma was observed.

Depending on the severity, allergic airway diseases such as asthma are associated with inflammation and airway obstruction. However, even if some symptoms might be comparable, the underlying principles causing the disease are different from chronic obstructive pulmonary disease (COPD). Nevertheless, a medication to both control allergy and to reduce inflammation would be of great general advantage.

In present medication of asthma one can be distinguished between fast acting and long term control. Short acting beta 2-adrenoceptor agonists (SABA), such as salbutamol are the gold standard in treatment of asthma symptoms. Anticholinergic medications such as ipratropium bromide provide addition benefit when used in combination with SABA in those with moderate or severe symptoms. Anticholinergic bronchodilators are an alternative if a person cannot tolerate a SABA.

For long term control, glucocorticoids are considered the most effective treatment available. Inhaled forms are usually used except in the case of severe persistent disease, in which oral steroids appear appropriate. Inhaled formulations may be used once or twice daily, depending on the severity of symptoms. Long acting beta-adrenoceptor agonists (LABA) have at least a 12-hour effect. They are however not to be used without a steroid due to an increased risk of severe symptoms and are thus challenged for additive value. Leukotriene antagonists such as montelukast or zafirlukast are an alternative to inhaled glucocorticoids, but are second line at present. Mast cell stabilizers such as cromolyn sodium are another but less potent alternative to glucocorticoids. Anti-immunoglobulin E (IgE) monoclonal antibodies constitute a relatively new but not yet broadly established potentially causal from of antiallergic medication.

Despite such advanced knowledge and various available mediation regimens, the increasing frequency of asthma is alarming. Rates of asthma have increased significantly between the 1960s and 2008 with 9% of US children suffering from asthma in 2001, compared with just 3.6% in 1980. The World Health Organization (WHO) reports that today 10% of the Swiss population suffers from asthma today compared with just 2% some 25-30 years ago. Thus, the establishment of alternative causal medication strategies is highly desirable and required.

Allergic airway diseases are not restricted to humans. Like human asthma, recurrent airway obstruction (RAO) in horses is considered a multifactor allergic airway hypersensitivity reaction elicited by environmental exposure to potential allergens (Robinson 2001) and heritable components (Gerber et al. 2009). Equine RAO has become one of the most common airway diseases (Fey 2006). Housing of horses in stables with permanent exposure to potentially allergenic organic and inorganic particles was reported to be a major trigger factor (Schmallenbach et al. 1998; Robinson 2001; Millerick-May 2009). Keeping horses on pasture leads to improved clinical signs, however, complete avoidance of allergens is not always possible (Robinson 2001). The permanent inhalation of various antigens from moldy hay, mite dust as well as endotoxin, β-glucan and other organic and inorganic particles causes airway neutrophilia and inflammation with a mixed Th1/Th2 immune response (Horohov et al. 2005; Cordeau et al. 2004). Although the clinical signs of RAO were well defined (Robinson 2001), immunological mechanisms are still controversy discussed. However, a predominant Th2 allergic response was recently presumed (Horohov et al. 2009). In several studies, signs of predominant Th2 response such as high IL-4, IL-5 in bronchoalveolar lavage fluid (BALF) of RAO horses exposed to antigens were reported (Lavoie et al. 2001; Cordeau et al. 2004). Due to persistent chronic inflammatory reaction in small airways of the affected horses, Th1 participation was also confirmed (Ainsworth et al. 2003).

Unmethylated Cytosin-Phosphate-Guanin-Oligodeoxynucleotides (CpG-ODN) were described as effective immune stimulating agents to cause a Th2/Th1 immune shift (Kline 2007). This shift further promoted an immunoglobuline isotype switch from IgE to IgG2 (Bohle 2002). The prevalence of IgE is a matter of ongoing debate (Halliwell et al. 1993; Marti 2009). In addition, a shift from pro-allergy mediating IL-4, IL-5 and IL-13 Th2 cytokines towards pro-inflammatory IFN-γ and IL-12 Th1 cytokines was discussed. Anti-inflammatory and antiallergic properties of Th2 cytokine IL-10 turned out to be of interest. Particularly, IL-10 producing T regulatory cells (Tregs) and its balance towards Th2 cells seems to play an important role in immune homeostasis (Akdis et al. 2004; Lloyd and Hawrylowicz 2009). Thus, one problem to be solved by the present invention is the clarification whether alternatively or in addition to the present conventional symptomatic therapy the possibility to modulate cytokine level in order to avoid development of an allergic hypersensitivity constitutes a promising option for use in the treatment of allergic and/or inflammatory lower airway diseases.

However, so far no decisive IL-10 regulating nanoparticulate composition comprising CpG-ODN has been proposed for use in therapy in allergic and inflammatory airway diseases, especially not my means of inhalation. Hence, there is a need for immunomodulating nucleic acids in a nanoparticulate composition for use in the treatment of allergic and/or inflammatory airway diseases such as asthma and RAO.

Three distinctive CpG classes (A-, B- and C-class) with varying immunologic effects were previously investigated (Krieg 2002). The key pattern-recognition receptor for these "danger signals" is the Toll-Like receptor 9 (TLR-9) which is located in endosomes (Krieg 2002). Recently, equine TLR-9 was detected in monocytes, airway epithelial cells, capillary endothelium in the lungs and pulmonary intravascular macrophages (Schneeberger et al. 2009). Furthermore, species-specific immune stimulation depending on CpG motifs has been determined (Hartmann and Krieg 2000; Rankin et al. 2001). US2004/0132682 claims an interesting method of treating inflammatory lung disease with suppressors of CpG-ODNs. However, these inflammatory lung diseases were explicitly not of allergic origin. The person of ordinary skill appreciates that the immunologic processes underlying allergic and non-allergic inflammatory inflammation of the lung are distinctive, e.g. concerning the involvement of neutrophils versus eosinophils.

Nevertheless, a promising immunotherapeutic strategy against allergic conditions of the upper airways including the nose as well as of the eyes already entering human clinical phase IIa studies involved CpG-ODN (Senti et al. 2009) as adjuvant, i.e. a synthetic analog of natural microbial CpG-ODN (Krieg 2002). This TLR9 agonist demonstrated some efficiency in treatment of allergic diseases if combined as an adjuvant with specific allergens due to CpG-DNA's potential to cause a Th2/Th1 shift (Vollmer and Krieg 2009, Kline 2007, Krieg 2002) which was associated with a downregulation of proallergic Th2 cytokines (IL-4, IL-5, IL-13) and an upregulation of antiallergic Th1 cytokines (IFN γ, IL-12) and an immunoglobulin isotype switch from allergy mediating IgE to IgG (Bohle 2002). U.S. Pat. No. 6,429,199 claims such CpGs as adjuvants in immunotherapy. The role of CpGs as adjuvants in order to stimulate the immune system is further supported by U.S. Pat. No. 7,488,490. However, despite for treatment of non-allergic lung diseases (US2004/0132682) such prior art rather teaches away from the employment of CpG-ODNs in monotherapy, especially for inhalation therapy, as inhalation of CpG-ODNs without immunotherapy did not result in a reduction of allergic clinical symptoms in a clinical trial (Fonseca et al 2009). Moreover, prior art is silent on an immunmodulating action based on IL-10 stimulation and especially, nanoparticles in no form are disclosed as eligible for use in related immunomodulating therapy, neither in general nor specifically for inhalative administration.

Pulmonary delivery as a non-invasive route of drug administration still constitutes a vivid research field in the treatment and diagnosis of respiratory and non-respiratory diseases (Smola et al. 2008). However, nanoparticulate delivery is still a partly unexplored field.

As an example for protein-based nanoparticles, gelatin nanoparticles (GNPs) from gelatin type A obtained from porcine skin were found to be immunologically inert and the use of GNPs showed amplified CpG-related TLR-9 activation for use as adjuvant in anticancer immunotherapy (Zwiorek et al. 2008). However, none such composition was ever evaluated in reducing the immune system's activity, for example for effective use in the treatment of allergic and/or inflammatory diseases. In detail, one problem to be solved is to identify a composition comprising the optimal immunomodulating agent to trigger specific immunomodulating effect such as Th2/Th1 shift and IL-10 stimulation and to reduce, for example, inflammation in clinical allergic symptoms known to the skilled person Compressor or jet nebulizers apparently are not suitable for nebulizing compositions comprising fragile nucleic acid such as CpG-ODNs even if jet nebulized protein-based nanoparticles such as from gelatin gave promising results such as enabling targeted lung cancer delivery of chemotherapeutic agent cisplatin (Tseng et al. 2007; Tseng et al. 2009). However, these compositions were much more stable than any nucleic acid comprising nanoparticulate composition. Tseng determined the median droplet size and lung deposition was proved in vivo, but no further characterization of the data of the nebulization process itself was given. US2005/019270 describes a method to nebulize spray-dried GNPs leaving the skilled person in doubt whether such methods destroys sensitive payload such as CpG-ODN. Against this technical background and the fact that the frequency of allergic and inflammatory airway diseases is still increasing, the problem is that there remains a tremendous need for new, long-lasting and efficient composition for use in causal prevention and/or treatment of allergic and inflammatory airway diseases.

SUMMARY OF THE INVENTION

In the present invention, the inventor surprisingly found that nanoparticulate compositions comprising various CpG ODNs and protein-based nanoparticles, respectively, are eligible for use in the prevention and/or treatment of allergic and/or inflammatory diseases of the lower airways. Moreover, the inventors found that such a composition exhibits a long-lasting therapeutic effect even after treatment has ceased. In addition, one single CpG ODN proofed to be sufficient as sole and main active ingredient in such a composition, preferably in a surprisingly low dose.

This was not taught or suggested by the prior art which, as explained above, revealed that certain ODNs, in particular CpGs, have distinctive effects on immune cells and are potentially useful as adjuvants for use in treatment of cancer and hypersensitivities even though it was known that CpGs can be used in compositions together with nanoparticles.

In a first aspect, the present invention provides a pharmaceutical composition comprising a pharmaceutically acceptable polymerized protein-based nanocarrier in the size range preferably between 150 to 300 nm and a preventative or therapeutic amount of an active agent, for use in the prevention and/or treatment of an allergic and/or inflammatory disease of the lower airways in a mammal, wherein the active agent is an oligonucleotide and/or an ODN which is effective for use in the prevention and/or treatment of an allergic and/or inflammatory disease of the lower airways, wherein the oligodeoxynucleotide is selected from the group consisting of guanidine phosphodiester cytosine (CpG) ODN class A, class B and/or class C, and wherein the active agent is coupled to the polymerized protein-based nanoparticle in a manner wherein the active agent maintains its preventive and/or therapeutic activity.

In a preferred embodiment of said aspect, the polymerized protein-based nanocarrier the pharmaceutical is a gelatin nanoparticle, an albumin nanoparticle, a legumine nanoparticle, a gliadine nanoparticle, an elastinlike polypeptide nanoparticle, a beta-galactoglobuline nanoparticle and/or a silk protein nanoparticle In a further preferred embodiment of said aspect, the pharmaceutical composition is a nebulizable aqueous dispersion or a nebulizable aqueous dispersion made from a lyophilisate.

In another preferred embodiment of said aspect, the aqueous dispersion is nebulized by a vibrating mesh nebulization device, wherein the resulting droplet size is preferably in the size range between 1 to 5 μm, wherein the respirable droplet fraction is 50 to 100%, wherein the nebulization efficiency is more than 95%, wherein the nanoparticle concentration within the aqueous dispersion is preferably in the range between 1.0 to 2.0 mg/ml, wherein the dispersant in the aqueous dispersion is highly purified water with a conductivity below 0.55 μS/cm or a physiological 0.9% NaCl solution, wherein the aqueous dispersion has a viscosity in the range between 0.85 and 1.1 mPa/s.

and wherein the nebulizable aqueous dispersion is nebulized by a vibrating mesh nebulization device at an output rate over 0.5 ml/min.

In yet another preferred embodiment of said aspect, said the comprised oligonucleotide and/or an ODN is administered at a dose of 0.0001 to 2 mg per kg body weight, preferably in a range between 0.0001 and 0.01 mg/kg body weight, most preferably in a range between 0.0002 and 0.001 mg/kg body weight.

Preferably the CpG ODN comprises a central palindrome CG motif-containing sequence flanked by a polyG sequence and a chimerical phosphodiester/phosphorothioate backbone.

In a preferred embodiment of said aspect, said CpG ODN is selected from the group consisting of 5'-CTG GTC TTT CTG GTT TTT TTC TGG-3' (SEQ ID NO: 1), 5'-G*G*G GGA CGA TCG TCG*G*G*G*G*G-3' (SEQ ID NO:2) wherein * indicate phosphorothioesters although a full phosphorothioate backbone is also disclosed for SEQ ID NO:2 in the present invention, 5'-TCG CGT GCG TTT TGT CGT TTT GAC GTT-3' (SEQ ID NO:3), 5'-TCG TCG TTT TGT CGT TTT GTC GTT-3' (SEQ ID NO:4), 5'-TCG TCG TTT TCG GCG CGC GCC G-3' (SEQ ID NO:5), 5'-TCG TCG TCG TTC GAA CGA CGT TGA T-3' (SEQ ID NO:6), 5'-GGTGCATCGATGCAGGGGGG-3'(SEQ ID NO:7), 5'-GGGGGGGACGATCGTCGGGGGG-3' (SEQ ID NO:8), 5'-GGGGGGGGACGATCGTCGGGGGGG-3' (SEQ ID NO:9), 5'-GGGGGGGGGACGATCGTCGGGGGGGG-3' (SEQ ID NO:10), 5'-GGGGGGGGGGACGATCGTCGGGGGGG-3' (SEQ ID NO:11), 5'-GGGGGGGGGGGACGATCGTCGGGGGGGGG-3' (SEQ ID NO:12), 5'-GGGGGGGGGGGGACGATCGTCGGGGGGGGGGG-3' (SEQ ID NO:13), and/or 5'-GGGGGGGGGGGGGACGATCGTCGGGGGGGGGGGG-3' (SEQ ID NO:14) and/or a derivative thereof comprising a chimerical phosphodiester/phosphorothioate backbone or a full phosphorothioate backbone. SEQ ID NO 2, 7, 8, 9, 10, 11, 12, 13 and 14 belong structurally to a common group of A-class CpG ODNs with altered G tails and backbones and are especially preferred.

In another preferred embodiment of said aspect, said CpG induces the release of antiallergic cytokine interleukin-10 and reduces the prevalence of proallergic and proinflammatory cytokines such as IL-4

In yet another preferred embodiment of said aspect, the mammal is a human, a primate, or a domestic animal or an animal for production, preferably a horse.

In still another preferred embodiment of said aspect, wherein the amount of oligonucleotide and/or an ODN is 0.1 to 10 wt %, preferably 1 to 7.5 wt % and more preferably 5 wt % in relation to the nanoparticle mass.

In a further preferred embodiment of said aspect, the pharmaceutical composition further comprises excipients selected from the group consisting of buffer salts, surfactants, lyoprotectors, dyes, chelating agents and/or radionuclides.

In another preferred embodiment of said aspect, the pharmaceutical composition is administrated to an individual via inhalation, wherein a vibrating mesh nebulization device is combined in such a way with an inhalation spacer in such a manner that the individual can inhale the nebulized pharmaceutical composition from the inhalation spacer, and wherein the vibrating mesh nebulization device is attached to the inhalation spacer, so that the nebulized pharmaceutical composition is quantitatively available at the inhalation spacer's top part nasal outlet.

In a further preferred embodiment, the composition of the present invention induces a prolonged clinical effect by reducing or inhibiting allergic and/or inflammatory symptoms and/or events in the lower airways and/or in the general state of health of the treated individual.

In yet still another embodiment of said aspect, the pharmaceutical composition is administered 1 time per day, 2 times per day, 3 times per day, 4 times per day, 5 times per day, 6 times per day, 1 time per week, 2 times per week, 3 times per week, 4 times per week, 5 times per week or 6 times per week, 3 times per months, 2 times per months or 1 time per month.

Preferably, the pharmaceutical composition of the present invention is administered in a cycle comprising a period of 3 to 14 d with 3 to 7 applications of the composition of claim 1, followed by an application free period of 7 to 84 d. The cycle is optionally succeeded by 1 to 100 further cycles, preferably by 1 to 5 cycles. The person skilled in the art is able to adopt the type or amount of cycles to the patient's individual needs.

In another preferred embodiment of said aspect, the pharmaceutical composition comprises a further antiallergic and/or anti-inflammatory active agent selected from the group consisting of glucocorticoids, H1-antagonists, leukotriene antagonists, mast cell stabilizers beta2 adrenergic receptor agonists and/or anticholinergic agents.

In a second aspect, the present invention provides a method for the production of the pharmaceutical composition comprises the steps of contacting the nanocarrier with the active ingredient in a ratio of preferably 90 to 99% nanocarrier to 1 to 9% active agent in a pharmaceutically acceptable medium, sensitive mixing, incubating for preferably 1.5 to 6 h optionally at a shaking rate of preferably 200 to 800 rounds per minute and 20 to 25° C., optionally purification by centrifugation at 10000 to 18000 g and adjusting the concentration to a nebulizable nanosuspension.

Figure 1:
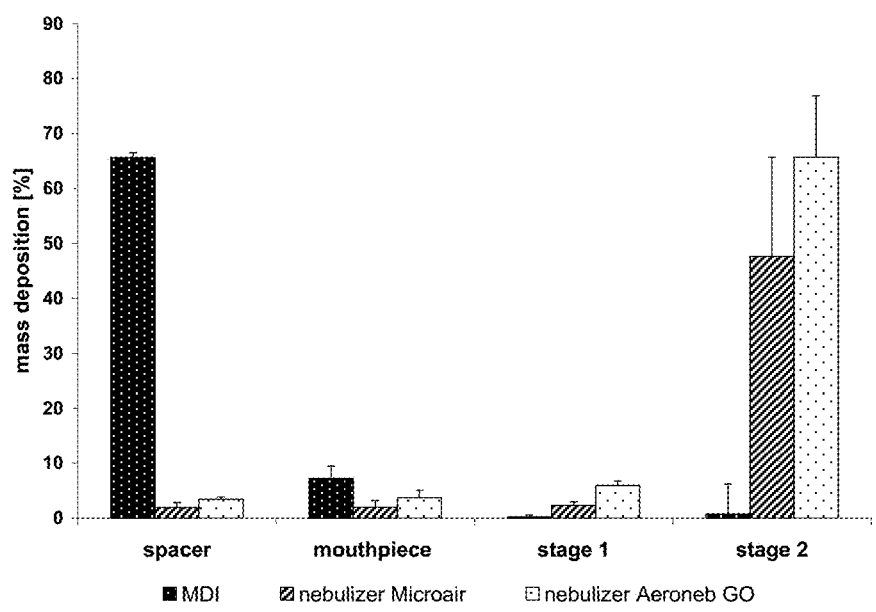
FIG. 1: Mass deposition of fluorescent labeled GNPs in the twin-stage impinger in dependence of the applied aerosolization device. Active VM devices surprisingly turn out to be preferred FIG. 2: IL-10 expression from BALF cells from healthy and RAO-affected horses with different CpG classes. BAL cells derived from RAO-affected horses (individuals n=7, measuring points n=3) (black bars) or health horses (individuals n=5, measuring points n=3) (white bars) were incubated with 13.5 μg of soluble CpG-ODN (A) or GNP-bound CpG-ODN (CpG-GNP) (B). Cells from healthy horses secreted significantly higher amounts of IL-10 than those of RAO-affected horses (P=0.0047). CpG 2216 A triggered the highest IL-10 release for both cells groups. Depicted values are group means±S.D. and corrected by subtraction of individual negative controls (untreated BAL cells).

FIG. 3: IL-4 expression from BALF cells from healthy and RAO-affected horses with different CpG classes. BAL cells derived from RAO-affected horses (individuals n=7, measuring points n=3) (black bars) or health horses (individuals n=5, measuring points n=3) (white bars) were incubated with 13.5 μg of soluble CpG-ODN (A) or GNP-bound CpG-ODN (CpG-GNP) (B). Cells from healthy horses secreted significantly lower amounts of IL-4 than those of RAO-affected horses (P=0.001) when treated with GNP-bound CpG-ODN (CpG-GNP) (B). Incubation with soluble CpG-ODN did not result in such significantly distinguishable release (A). Depicted values are group means±S.D and corrected by subtraction of individual negative controls (untreated BAL cells) which particularly resulted in negative values. The original IL-4 ELISA results were positive before correction.

FIG. 4: Technical setup of a VM-device 1 combined with the equine inhalation spacer 2, wherein a 100 ml glass connecting adapter 3 with two ground joints, for example, in a 90° angle is connected to the medication holding container 4 attached to the aerosol generator unit 5 (nebulizer) e.g. by a wider joint such as a 29/32 joint 6, known to the skilled person. The tighter joint, e.g. a 19/26 joint 7 known to the skilled person, is inserted into a rubber seal 8 on the inlet 9 of the employed inhalation spacer 2, e.g. a spacer with an inhalation mask 10 or an inhalation spacer with nose adapter.

FIG. 5: Release of key cytokines from BALF cells gained from RAO-affected horses stimulated in vitro by ODN and ODN-GNP before (pre) and after (post) in vivo inhalation therapy, respectively. a, IL-10 release from cell cultures stimulated by soluble ODN and ODN-GNP is increased by inhalation therapy of GNP-bound ODN and subsequent in vitro stimulation (n=18, ±S.D) by 6 different GNP-bound ODNs or by 6 different soluble ODNs on average. b, IL-4 release is accordingly decreased.

FIG. 6: Effect of GNP-bound CpG-ODN and plain GNPs on cytokine release in vivo before and after inhalation therapy. a, IL-10 release is expressed as n-fold increase based on 1 as initial value before inhalation. IL-10 release from RAO-affected horses (n=4, ±S.D.) before and after three and five inhalation of GNP-bound CpG-ODN (black bars), from healthy horses (n=4, ±S.D.) before and after three inhalations of GNP-bound CpG-ODN (grey bars) and from healthy horses (n=4, ±S.D.) before and after three inhalations of plain GNP (white bars). b, IFN-g(amma) release from RAO-affected horses before and after three and five inhalation of GNP-bound CpG-ODN (black bars) and from healthy horses before and after three inhalations of plain GNP (white bars).

FIG. 7: Therapeutic effect of GNP-bound CpG-ODNs versus plain GNPs (placebo) on important clinical parameters. a, Breathing rate before and after treatment by GNP-bound CpG-ODN in RAO-affected horses (n=4, ±S.D.), before and after treatment by GNP-bound CpG-ODN in healthy horses (n=4, ±S.D.) and before and after treatment by GNPs (placebo) in healthy horses (n=4, ±S.D., left to right). b, Oxygen partial pressure in arterial blood before and after respective treatments. c, Occurrence of tracheobronchial secrete before and after respective treatments. d, Percentile of neutrophil granulocytes in the TBS before and after respective treatments.

DETAILED DESCRIPTION OF THE INVENTION

Definitions

In the context of this specification, the term "protein-based nanoparticle", refers to discrete, dispersible particles in the size range 1 to 1000 nm consisting of pharmaceutically acceptable proteins. The proteins and the resulting particles are biocompatible, biodegradable without significant pro-allergenic potential or any toxic properties, both of the protein and its resulting nanoparticle as well as of its degradation products.

In the context of this specification, the term "gelatin nanoparticle" (GNP) refers to a protein-based nanoparticle polymerized from gelatin produced by desolvation. Nanoparticles prepared by a two step desolvation technique and subsequent chemical cross-linking (Coester et al. 2000) maintain their non-toxic properties while featuring a higher storage stability than liposomal liquid formulations and good in vivo stability upon administration (Coester et al. 2006).

In the context of this specification, the term "gelatin" refers to a natural polymer derived from porcine, bovine or fish collagen recognized as a biodegradable and biocompatible starting material being in use as plasma expander for decades (Ward et al. 1977). Alternative, recombinant gelatin can be used. It is obtained mainly by acidic (A-type) or alkaline (B-type), but also thermal or enzymatic degradation of the collagen. Collagen forms 30% of all vertebrate body protein with a majority in bone and skin. While gelatin and the delivery systems based on this polymer are biocompatible and biodegradable without toxic degradation products (Tabata and Ikada 1998; Kawai et al. 2000; Yamamoto et al. 2001; Ward et al. 1977), they are since a long time known for high physiological tolerance and low immunogenicity. The overall beneficial properties of gelatin contributed to its proven record of safety as food supplement which is also documented by the classification as "Generally Recognized as Safe" (GRAS) by the US Food and Drug Administration (FDA). Moreover, intravenously administered applications like plasma expanders (e.g. Gelafundin™, Gelafusal™) consist of gelatin derivatives.

In the context of this specification, the term "lower airways" is directed to the respiratory brochioles and alveolar sacs (Weibel and Gomez 1962) which offer a large surface area for drug interaction and are the stage of several immunologic actions decisive in allergic and/or inflammatory diseases of the respiratory system.

In the context of this specification, the term "CpG oligodeoxynucleotides" refers to short, preferably 20 to 34 bases long artificial, unmethylated sequences featuring cytosine poly guanine palindromes. They are agonists for a member of the pattern recognition receptor (PRR) family signalling through an endosomal membrane based type receptor, the Toll-Like Receptor 9 (TLR9) (Angel et al. 2008; Wernette et al. 2002). CpGs were shown to influence several signalling pathways in a variety of immune cells, leading to cytokine production in many mammalian species (Zwiorek et al. 2004; Zhao et al. 2010). It appears that the specific purines and pyrimidines surrounding the CpG motif, phosphothioated backbone, as well as the spacings between CpG motifs may influence both the level and the type of immune stimulation (Krieg et al. 1995; Mutwiri et al. 2003). CpG motifs improve the antigen presenting function of dendritic cells (DCs), monocytes and macrophages, induce the proliferation of B lymphocytes, stimulate the immunoprotective activity of natural killer (NK) cells, and recruit T cells to the site of ODN administration (Torchilin 2007; Zwiorek et al. 2008). Recent studies showed that the immune system responds to CpG motifs by activating potent Th1-like immune responses which can be harnessed for immune therapy of cancer, allergy, infectious diseases (Krieg 2002), autoimmune diseases, and sterile inflammation (Kanzler et al. 2007). Consequently, CpGs may also be used as potent adjuvant for vaccines in prophylactic anticancer studies involving GNP-bound CpG (Bourquin et al. 2008).

In the context of this specification, the term "A-class" refers to a ODN sequence wherein the CpG are phosphodiesters in palindrome, while the 3' and 5' tail-guanidines are phosphothioesters, wherein monomers can associate to tetrads due to G-tail association, and wherein the ODN sequence strongly induce plasmoidal dendritic cell IFN-alpha secretion, while B-cell proliferation is poorly induced. Within the context of this specification, the whole sequence backbone may consist of phosphothioesters.

In the context of this specification, the term "B-class" refers to a ODN sequence wherein the backbone is fully phosphothioate and linear. B-cell proliferation and pDC maturation is strongly induced.

In the context of this specification, the term "C-class" refers to a ODN sequence wherein the backbone is phosphothioate and a 3' palindrome forms duplexes and wherein the sequence has intermediate effects of both A- and B-class.

In the context of this specification, the term "immunomodulating" refers to the normalization of an otherwise (atopic) disorder of the immune system. By means of the present invention, IL-10 levels in the lower airways and in the blood are increased to and/or maintained at such levels which are typical for individuals not suffering from any allergic and/or inflammatory disease of the lower airways. Hence, immunomodulating relates, in consequence, to the amelioration or improvement of clinical symptoms related to allergic and/or inflammatory diseases of the lower airways. Thus, "immunomodulating" has to be distinguished from "immunostimulating" which has to be understood in a way to selectively or unselectively promote certain immune cells for action and/or interaction, such as release of inflammatory cytokines. In general, an immunomodulator, is a substance, e.g. a drug, which has an effect on the immune system. The skilled person is aware of the fact that most drugs do not have effects on only one receptor, so an immunomodulator may be at the same time an immunosuppressant and an immunostimulant, on different targets within the immune system.

However, in the context of the present application, an immunomodulating composition is understood to comprise tolerogens, such as CpG ODNs which trigger IL-10 release from various immune cells, preferably in the lower airways, and induce regulatory T cells. They induce tolerance and make the tissue, i.e. the lower airways, non-responsive to respective antigens. Tolerance is understood as the state of non-responsiveness to respective antigens In the context of this application, a "prolonged" effect relates to a measurable tolerance which persists even as the treatment has ceased. In detail, clinical symptoms of an allergic or inflammatory disease of the lower airways remain significantly reduced after treatment has ceased, such as at least 2 weeks after the last medication was administered, preferably 4 weeks, most preferably 12 weeks.

In the context of this specification, the term "nebulizable" refers to a composition, preferably an aqueous nanoparticle dispersion, whose physicochemical characteristics are such, that employment of an appropriate nebulizing device, preferably a vibrating mesh nebulizing device, leads to a nearly quantitative nebulization efficiency and an output rate high enough to guarantee feasible use with an individual. Moreover, the concentration of the nanoparticle dispersion is such that the viscosity is not too high to block the nebulizer. Likewise, nebulizable requires that the nanoparticles are small enough not to block the nebulizer. This includes the absence of agglomerates or aggregates in the nanoparticle dispersion, expressed by a low PDI.

In the context of this specification, the term "vibrating mesh (VM)" refers to passively VM devices such as the Omron Microair nebulizer which can be distinguished from active VM devices such as the AeroNeb Go of Nektar (Ghazanfari et al. 2007a). The first group featured a perforated plate with approximately 3 µm-diameter holes. The plate is passively induced by an attached piezo crystal via a transducer horn. The fluid gets extruded through the microholes and consequently, the aerosol is formed with very high nebulized drug output efficiency and, however, relatively low output rates when viscous formulations were involved. Conversely, the actively VM devices featured a plate with dome-shaped apertures which are moved up- and downwards $10^5$ times per second in a micrometer range by an electric vibrating element. This micropump extrudes the fluid and thus created the aerosol (Ghazanfari et al. 2007a). Described advantages of the active VM device were a more rapid aerosol generation and a relatively high nebulized output over 70%.

In the context of the specification, the term "VM nebulization device is attached to the inhalation spacer" refers to a functional combination of the VM nebulizer with an inhalation spacer suitable for the individual to receive the composition. To facilitate aerosol delivery in vivo, e.g. a 100 ml glass connecting adapter with two ground joints, for example, in a 90° angle is connected to the medication holding container attached to the aerosol generator unit (nebulizer) e.g. by a wider joint such as a 29/32 joint, known to the skilled person. The tighter joint, e.g. a 19/26 joint known to the skilled person, is inserted into the rubber seal on the inlet of the employed inhalation spacer, e.g. a spacer or inhalation mask for humans or an inhalation spacer with nose adapter such as the Euquinehaler® (Equine Health Care, Horsholm, Denmark) or a mouth fully covering mask. This combination provided an easy applicable device for rapid equine nanoparticulate therapeutics inhalation.

In the context of this specification, the terms "treatment" and "treating" refer to any and all uses which remedy a condition or disease or symptoms thereof, prevent the establishment of a condition or disease or symptoms thereof, or otherwise prevent or hinder or reverse the progression of a condition or disease or other undesirable symptoms in any way whatsoever.

In the context of this specification, the term "therapeutically effective amount" includes within its meaning a non-toxic amount of B-guanidinopropionic acid sufficient to provide the desired therapeutic effect. The exact amount will vary amongst others from subject to subject depending on the age of the subject, the gender, the ethnic origin, their general health, the severity of the disorder being treated and the mode of administration. It is therefore not possible to specify an exact "therapeutically effective amount". However one skilled in the art would be capable of determining a "therapeutically effective amount" by routine trial and experimentation.

In the context of this specification, the term "allergy" is directed to type I hypersensitivities (also called immediate hypersensitivity), which are characterized as rapidly developing reactions of the immune system to a trigger. Preferably, said term is directed to essential hypertension. More preferably, said term is directed to essential arterial and/or essential pulmonary hypertension.

In the context of this specification, the term "cross-linked" refers to the stabilization of protein-based nanoparticles produced by desolvation or coacervation. Thereby single protein chains are permanently and covalently bound together to prevent early disintegration. Cross-linking may be facilitated by appropriate enzymes chemical agents.

In the context of this specification, the term "polydispersityindex (PDI)" refers to a dimension-less unit to characterize distribution ranges providing normal distribution is given for the data set to be evaluated. Preferably, the PDI is eligible to characterize particle size distributions and is used as a quality assessment parameter. A PDI value below 0.1 stands for monodispersity or a very narrow particle size distribution, a PDI value between 0.1 and 0.15 stands for a narrow particle size distribution, a PDI value between 0.15 and 0.25 stands for a broad particle size distribution, while a PDI value between 0.25 and 1.0 stands for a very broad particle size distribution or polydispersity.

In the context of this specification, the term "anti-allergic" is defined to mean an amount of the nanoparticle-active agent comprising composition that is capable to significantly reduce the clinical symptoms and the immunologic parameters of a person with an allergic disease.

The term "anti-allergic agent" refers to a pharmaceutical composition comprising the nanocarrier and the anti-allergic ingredient such as an Immunomodulating CpG ODN which is efficient for use in the treatment of allergic diseases, especially of those affecting the lower airways and which are associated with inflammatory events.

The term "nanocarrier" refers to a pharmaceutically acceptable means in the nanometer range of formulating the active agent to allow the active agent to perform its pharmacological action on the desired physiological site.

The term "adjuvant" refers to a pharmaceutically acceptable means of actively or passively enhancing the active ingredient's interaction with the desired physiological target.

PREFERRED EMBODIMENTS

Compositions comprising nanoparticles and active agents, preferably nucleic acid active agent, administrated preferably via inhalation, e.g. by a VM device, for use in airway anti-allergic and anti-inflammatory therapy were not previously reported in prior art.

Previously, jet nebulizers and other devices were used to nebulize protein-based nanoparticles, such as GNPs. However, these devices exercise huge sheer forces on the particle surface and, hence, are potentially detrimental to sensitive payload such as nucleic acids. Yet, the inventors surprisingly found that nebulizing by VM devices, which still exercise some mechanical stress on the nebulized material, is tolerated, for example, by sensitive CpG-ODNs of the present invention which retain their immunomodulating properties even after nebulization. Therefore, two established devices with different VM techniques, active and passive, were compared in addition to the pMDI for GNP integrity, its impact on various parameters' influence of viscosity, its importance of administration time and recovered concentration after quantitative recondensation to meet the needs for a convenient application of the inventive composition of the present invention.

Surprisingly, preferably nanoparticulate CpG-ODN compositions administrated via inhalation, such as by a nebulization device known in the art, preferably. by a VM device, most preferably by an active VM device, showed an anti-allergic and anti-inflammatory action when employed as sole active agent in contrast to prior art, wherein CpG-ODNs were only used as adjuvants, and, even more, not used in inhalation therapy in a nanoparticulate formulation. Therefore, the invention relates to nanoparticulate nucleic acid active agent compositions for use in the prevention or treatment of allergic and/or inflammatory airway diseases in an individual, preferably in a mammal, more preferably in a human, horse, dog, cat, cow, pig, sheep, goat, mouse, rat, gunny pig, elephant, camel, giraffe, hippopotamus and the like, most preferably in a human or horse.

The invention relates to a composition wherein the active ingredient is efficient for use in prevention and/or treatment independent from the allergen. Hence, active agent nucleic acid monotherapy provides the advantage of antigen-independent treatment of a broad spectrum of allergic individuals. Thus the composition of the present invention for use in prevention and/or therapy such as inhalation therapy of allergic and/or inflammatory diseases of the lower airways and the like is superior over individual antigen desensibilization therapies and the like in terms of practicability and applicability.

The invention further relates to a method for the prevention (prophylaxis) or treatment of allergic and/or inflammatory airway diseases in a subject in need thereof comprising administration to the subject of a therapeutically effective amount of nanoparticulate nucleic acid active agent compositions, as defined above, wherein the method is characterized in that the nanoparticulate nucleic acid active agent compositions is taken up by competent immune cells and/or epithelium cells located in the lower airways, wherein the nanoparticulate nucleic acid active agent compositions comprise CpG ODNs, preferably class-A, class-B and/or class-C CpG ODNs, more preferably class-A CpG ODNs, even more preferably CpG wherein the nanoparticulate nucleic acid active agent compositions comprise the SEQ ID NO:1, 2, 3, 4, 5, 6, 7, 8, 9, 10, 11, 12, 13 and/or 14, preferably SEQ ID NO:2. with a fully phosphothioate backbone and/or SEQ ID NO:7 with a full phosphothioate backbone and/or SEQ ID NO:8, 9, 10, 11, 12, 13 and/or 14 with a chimerical phosphodiester and phosphothioate backbone (the poly G 3' and 5' tail regions), even more preferably SEQ ID NO:2 with a chimerical phosphodiester and phosphothioate backbone (the poly G 3' and 5' tail regions) and/or SEQ ID NO:8, 9, 10, 11, 12, 13 and/or 14 with a full phosphothioate backbone.

The pharmaceutical composition of the present invention is eligible for use in the prevention of aforementioned diseases and associated events because of its Immunomodulating properties. In the context of the invention, immunomodulating refers to the normalization of an otherwise (atopic) disorder of the immune system. By means of the present invention, IL-10 levels in the lower airways and in the blood are increased to and/or maintained at such levels which are typical for individuals not suffering from any allergic and/or inflammatory disease of the lower airways.

In a preferred embodiment of the present invention, the protein-based nanoparticles of the pharmaceutical composition are of such a size that they are both recognized by the immune competent cells they target in the lower airways and, at the same time, do neither block the alveolar airways or any other part of the respiratory tract nor cause any other adverse or repelling reaction. It was shown, that immunomodulating activity is best supported on the one hand and nanotoxicological threats are not an issue on the other hand in the size range of 1 to 1000 nm, preferably 100 to 350 nm, more preferably 150 to 300 nm, most preferably 200 to 250 nm, while the PDI is preferably 0 to 0.15 and most preferably 0 to 0.1. Hence, the size and size distribution of the nanocarriers disclosed in the present invention do contribute decisively to the immunomodulating effect of the surprising composition. The nanocarriers may also contribute to a sustained release of the active agent at the site of interaction with competent immune cells in the lower airways.

Pharmaceutical compositions within the scope of the present invention are preferably for inhalative administration although other ways of application might be possible such as parenteral like intravenous, subcutaneous or intramuscular application of a corresponding sterile formulation or a specialized formulation suitable for transdermal or peroral delivery.

The protein-based nanocarriers of the present invention are preferably nanoparticles made from pharmaceutically acceptable, biocompatible and biodegradable proteins selected from the group consisting of, albumine, gelatin, legumine, gliadine, elastinlike polypeptide, beta-galactoglobuline and/or silk protein.

Preferably, the protein-based nanocarriers are produced by a coacervation process. Due to relatively mild conditions the coacervation or equally coined desolvation process is the most appropriate and frequent method to prepare protein-based nanoparticles. Therein, a colloidal system is created when the solvent in which the protein was initially dissolved is gradually extracted into an anti-solvent phase. Thereby a phase separation occurs which results in a phase of solid colloid dispersed in a second phase consisting of the anti-solvent and the initial solvent (Weber et al. 2000). Consequently, solvent and anti-solvent must be miscible such as water as solvent and ethanol or acetone as anti-solvent whereof the latter was often used to produce GNPs by a two step desolvation technique (Coester et al. 2000; Langer et al. 2003). While a stable size is reached after an initial process period the further addition of anti-solvent leads to increased particles yield in the course of desolvation (Weber et al. 2000). Furthermore, the pH value of the protein solution prior to desolvation has an impact on the resulting particle size and yield due to higher probability of protein coacervation at net-zero surface charge at the isoelectric point, which applies to gelatin, HSA, BSA and B-lactoglobulin.

In a preferred embodiment, the composition may comprise active targeting moieties to target the particles with the active agent to a desired body site for specific and/or causal treatment. This may include receptor, antibodies or fragments or hybrids thereof.

In another preferred embodiment, the protein-based nanoparticles are chemically or enzymatically cross-linked. For use in therapeutic applications, cross-linked nanoparticles are of special importance to guarantee sufficient stability and/or integrity over the required period of intended activity and/or employment. The protein may be chemically cross-linked by formaldehyde, dialdehydes, isocyanate, diisocyanate, carbodiimide, alkyldihalogenides and/or glutharaldehyde. Alternatively, enzymatic cross-linking can be performed which is an attractive approach due to the high specificity of the enzyme catalysis controllable to a certain degree by changing pH and temperature.

Preferably, transglutaminase or laccase is used in the cross-linking of protein-based nanoparticles. However, microbial transglutaminase is especially preferred.

In a very preferred embodiment, glutaraldehyde is used to cross-link protein-based nanoparticles (Weber et al. 2000), as no toxic side reactions or gelatin-associated immunity reactions were observed (Zwiorek 2006). As glutaraldehyde is consumed during the GNP cross-linking reaction and residuals are removed by particle purification, consequently no adverse effects could be observed.

The compositions may conveniently be presented in unit dosage form and may be prepared by any of the methods well known in the art of pharmacy. All methods include the step of the nucleic acid active agent as defined herein into association with a carrier which constitutes one or more accessory ingredients. In general, the compositions are prepared by uniformly and intimately bringing into association the β-guanidinopropionic acid with a nanocarrier and then, if necessary, shaping the product into the desired composition.

Remarkably, the composition of the present invention exhibited a prolonged effect in significantly ameliorating or inhibiting clinical expression of allergic and/or inflammatory diseases of the lower airways. The prolonged effect of at least 4, preferably 12 weeks allows for regimen cycles with long regimen-free periods. This administration scheme increases compliance and is less impairing the patient's quality of life. In addition, chronic side effects of the composition of the present invention are avoided.

Surprisingly, a relatively low dose of the present composition was found to be effective for use in the prevention and/or treatment of allergic and/or inflammatory diseases of the lower airways. Previous in vivo studies involving CpG as adjuvant ranged from s.c. 100 μg per mouse, i.e. 5000 μg per kg body weight (Bourquin 2008) to 300 μg per human in a clinical trial, i.e. about 4.5 μg per kg body weight (Senti 2009). In the present study, significantly lower concentrations were found to be effective for the above-identified uses, for example 0.1, 0.2, 0.3, 0.4, 0.5, 0.6, 0.7, 0.8, 0.9 and/or 1.0 μg per kg body weight. The skilled person appreciates that lower dosage is associated with a lower risk of side effects, which even allows treatment of such a subpopulation of patients which otherwise would not have been eligible for treatment involving an immunomodulating composition. Additionally, lower amounts per dosage result in lower prices per application, which is of advantage especially with regard to expensive nucleic-acid-based drugs.

Generally, an effective dosage of the nucleic acid active agent present in the pharmaceutical composition of the present invention is in the range of about 0.0001 to 2 mg per kg body weight, preferably in a range between 0.0001 and 0.01 mg/kg body weight, most preferably in a range between 0.0002 and 0.001 mg/kg body weight. More typically, an effective dose range is in the range of 0.0001 to 2 mg per kg body weight, preferably in a range between 0.0001 and 0.01 mg/kg body weight, most preferably in a range between 0.0002 and 0.001 mg/kg body weight per 72 hours; about 0.0005 mg to about 0.05 mg per kg body weight per 72 hours, or about 0.005 mg to about 0.02 mg per kg body weight per 72 hours.

Compositions comprising the nucleic acid active agent or a pharmaceutically acceptable salt or derivative thereof may contain an amount of said nucleic acid of 0.1 to 10 wt %, preferably 0.5 to 5 wt %, more preferably 1 to 5 wt % and still more preferably at 5 wt %.

Compositions comprising the nanoparticle-nucleic acid active agent composition suitable for oral administration may be present as discrete solid dosage forms such as gelatine or HPMC capsules, cachets or compressed tablets, each containing a predetermined amount of the nanoparticle-nucleic acid active agent composition, as a powder, granules, as a solution or a suspension in an aqueous liquid or a non-aqueous liquid, or as an oil-in-water liquid emulsion or a water-in-oil liquid emulsion.

Compositions for parenteral administration include aqueous and non-aqueous sterile nanosuspensions which may contain anti-oxidants, buffers, bacteriostats and solutes which render the formulation isotonic with the blood of the intended recipient, and which may include suspending agents and thickening agents. A parenteral composition may comprise a cyclic oligosaccharide such as hydroxypropyl-$\beta$-cyclodextrin. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use.

Compositions suitable for transdermal administration may be presented as discrete patches adapted to remain in intimate contact with the epidermis of the recipient for a prolonged period of time. Such patches suitably comprise the nanoparticle-nucleic acid active agent composition as an optionally buffered aqueous suspension of, for example, 0.01 M to 10 M, more preferably 0.05 to 1 M, even more preferably 0.1 M to 0.2 M concentration with respect to the compound. Such patches may liberate the contained pharmaceutical preparation from the reservoir membrane- or matrix-controlled.

Aerosol compositions for delivery to the lung by inhalation may, for example be formulated as solutions or suspensions, preferably aqueous suspensions or solutions and/or suspensions in liquefied propellant delivered from pressurised packs, such as a metered dose inhaler, with the use of a suitable liquefied propellant. Suitable propellants include a fluorocarbons or a hydrogen-containing fluorocarbon or mixtures thereof, particularly hydrofluoroalkanes. The aerosol composition may be excipient free or may optionally contain additional composition excipients well known in the art, such as surfactants e.g. oleic acid or lecithin and/or cosolvents e.g. ethanol. Pressurised compositions will generally be retained in a canister (e.g. an aluminium canister) closed with a valve (e.g. a metering valve) and fitted into an actuator provided with a mouthpiece.

Alternatively, a dry powder preparation of the nanoparticle-nucleic acid active agent composition can be used to administer said formulation as a dry powder inhaler without propellants and a related suspension formulation.

Medicaments for administration by inhalation desirably have an optimum particle size for inhalation into the bronchial system is usually 1-10 μm, preferably 1-5 μm to target the alveolar sacs. Particles having a size above 20 μm are generally too large when inhaled to reach the small airways. When the excipient is lactose it will typically be present as milled lactose, wherein not more than 85% of lactose particles will have a mass mean diameter (MMD) of 60-90 μm and not less than 15% will have a MMD of less than 15 μm.

Figure 4:
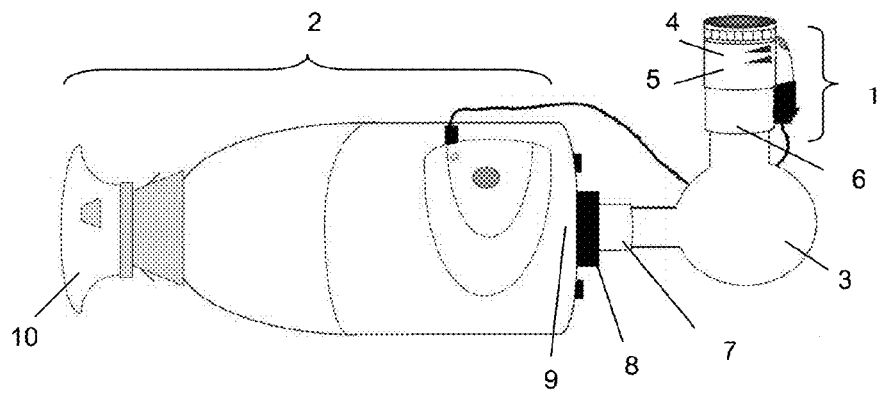

Nebulization of the pharmaceutical composition for subsequent inhalation is facilitated preferably by a VM device, more preferably by an active VM device. Most preferably, this active VM is connected to an inhalation spacer to ease intake of the nebulized pharmaceutical composition, especially for administration to individuals like infants and animals (FIG. 4). Such connection is preferably reversible and is between the active VM device and is performed by connecting a top preferably 29/32 ground joint of a glass connector with two ground joints situated in a 90° angle. Moreover, the 19/26 ground joint at the other opening side of the glass connector is introduced reversible into the rubber seal of an equine inhalation spacer. The skilled person will acknowledge that joint and/or connector combinations will be required that specifically and exactly fit into the active VM devices employed in every individual case.

Preferably, the nebulizer in the context of the present invention is an active VM nebulizer which keeps the nanoparticle-bound delicate nucleic acid active agent in its biologically active form without destroying it by shear forces or other negative influence upon the nebulisation process.

The nucleic acid active ingredient is bound to the surface of the protein-based nanocarrier reversibly via electrostatic interaction. However, interaction is strong enough to keep the nucleic acid active ingredient on the nanocarrier surface until interaction with immune competent cells in the lower airways.

The compositions may incorporate a controlled release matrix that is composed of sucrose acetate isobutyrate (SAIB) and organic solvent or organic solvent mixtures. Polymer additives may be added to the vehicle as a release modifier to further increase the viscosity and slow down the release rate.

The co-administration of the nanoparticle-nucleic acid active agent composition or a pharmaceutically acceptable salt thereof or a derivative thereof and one or more further anti-allergic and/or anti-inflammation agents may be simultaneous or sequential. Simultaneous administration may be effected by nanoparticle-nucleic acid active agent composition being in the same unit dose as the anti-allergic and/or anti-inflammation agent, or nucleic acid active agent and the anti-allergic and/or anti-inflammation agent may be present in individual and discrete unit doses administered at the same, or at a similar time. Sequential administration may be in any order as required. The anti-allergic and/or anti-inflammation agent may be selected from the group consisting of glucocorticoids, H1-antagonists, leukotriene antagonists, mast cell stabilizers beta2-adrenergic receptor agonists, anti-IgE antibodies or fragments thereof and/or anticholinergic agents, as explained above in detail for the fast acting and long term control medication of asthma.

All publications mentioned in this specification are herein incorporated by reference. The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be further described in greater detail by reference to the following specific examples, which should not be construed as in any way limiting the scope of the invention.

EXAMPLES

Example 1

Preformulation Studies on a Nebulizable Immunomodulating Nanoparticulate Composition Materials Gelatin A Bloom 175, Glutaraldehyde 25% solution, cholamine and EDC were purchased from Sigma (Taufkirchen, Germany), fluorescent dye Alexa 488 was obtained from Invitrogen (Carlsbad, USA). The immunomodulative single stranded mixed phosphothioester/-diester backbone CpG-ODN class A with the sequence 5'-G*G*GGGACGATCGTCG*G*G*G*G*G*-3' (SEQ ID NO:2) was received as lyophilisate from biomers (Ulm, Germany), diluted in sterilely filtrated highly purified water (HPW) produced by a purelab plus device (Elga labwater, Celle, Germany) to a final concentration of 1 mg/ml and stored at −80° C. till final use. IL-10 quantifying equine Duo set ELISA was purchased from R&D Systems (Minneapolis, USA). Liquefied gas propellant HFA 134a was obtained from Schick GmbH (Stuttgart, Germany).

Preparation of the CpG-GNPs

Plain, cationized and fluorescent labeled GNPs were prepared according to the established protocols (Coester et al. 2000; Zwiorek et al. 2008). 20 bases long CpG-ODN 2216 (Biomers, Ulm, Germany) was loaded onto the GNP surface in HPW by electrostatic attraction. To ensure colloidal stability, the CpG concentration was set to 5% (m/m) based on the GNP mass. For this, the aseptically prepared samples of cationized GNPs were subsequently incubated for 1 h at 22° C. and 300 rpm using a Thermomixer™ device (Eppendorf, Hamburg, Germany). The concentration of the GNP dispersion was set to 0.5, 1.0 or 1.5 mg/ml for subsequent different nebulization setups.

Determination of Nanoparticle Properties and Dispersion Viscosity

Particle sizes were determined by dynamic light scattering (DLS) using a Zetasizer Nano ZS (Malvern Instruments, Worcestershire, England). Nanoparticles were diluted in HPW and measured in concentrations below 0.1 mg/ml at 25° C. Thus, any influence of viscosity and of unlikely multiscattering on the results was ruled out. Intensity weighted particle mean diameter (Z-average) and polydispersity index (PDI) as the width of the fitted Gaussian distribution were calculated by the DTS V. 5.10 software from at least 15 subruns. All measurements were performed at least in triplicate. For Zeta potential measurement before and after loading GNPs were diluted in 10 mM NaCl to maintain a sufficient but not too high ionic strength in terms of conductivity and electrode corrosion. GNP concentration was determined gravimetrically with a Mettler Toledo UMX2 (Mettler, Greifensee, Switzerland). Viscosity of GNP formulations was determined by an automated microviscosimeter (AmV) device by Anton Paar GmbH (Graz, Austria).

Percentile loading efficiency was proven indirectly by UV-spectroscopy at 260 nm wavelength (UV1, Thermo Fisher Scientific Inc., Waltham, USA) Therefore, the supernatant(s) of CpG-GNP samples, supernatants of GNP controls (without CpG) and supernatants of CpG controls (without GNP) were taken into account as given below:

$$CpG\ loading = \left(1 - \left(\frac{OD\ of\ s(CpG-GNP) - OD\ of\ s(GNP\ control)}{OD\ of\ s(CpG\ control)}\right)\right) \times 100\ [\%]$$

GNP Aerosolization

For aerosolization by pMDIs, 12 ml aluminum pMDI containers were filled with 3, 5 or 10 g of a 1 mg/ml GNP dispersion and a cap with dosing chamber and purging valves was positioned on top of the container. Crimping and subsequent liquefied propellant filling trough the dosing chamber was conducted by a hand operated laboratory plant 2005/2 (Pamasol, Pfaeffikon, Switzerland). The filling weight of propellant was kept constant at 1.5 g/pMDI resulting in 2:1, 4:1 and 8:1 GNP dispersion:propellant ratios. To estimate consistency of dosing, a sequence of 30 spraying passes was performed for each formulation and the pMDI was weighted after each pass. Aerosols and droplets were collected in suitable 50 ml tubes for subsequent GNP characterization.

VM-nebulization was performed by a passive VM such as NE-U22V Microair®(Omron, Matsusaka, Japan) and or actively VM such as AeroNeb Go® (Aerogen, Galway, Ireland) device. The Passive VM device instrument was employed with the manufacturer-provided rubber supplement mouth piece while the Active VM device was either (a) used with the manufacturer-provided "nebulizer body" connected to the essential medication cup/aerosol generator part or with a 90° glass connector with joints that suitably matched the medication cup/aerosol generator part's outlet side. Nebulization efficiency (NE) was determined for all three instrumental setups by weighing the VM device before nebulization and after operation to dryness. The latter was considered apparent when visibly no more vapor escaped from the aerosol generator. After division of the weights, the results were given in percent. To determine the post-nebulization weight, the whole instrument with all practically relevant adapters or nebulizer bodies was taken into account. Therefore, only those portions of the nebulized formulation that completely escaped the apparatus and consequently contributed to the deposition study were considered relevant for the NE calculation.

For size and concentration evaluation of post-nebulized GNPs, the resulting aerosol was collected in a closed glass system equipped with a water cooled chiller at 4° C. to quantitatively condensate vapors. An applied vacuum of 700 mbars which translated to a flow rate of approximately 30 l/min (Vaccubrand CVC200, Wertheim, Germany) was introduced to assure high yields of GNP dispersion in the collection round bottom flask.

Subsequently, intercepted samples were analyzed for size, size distribution and concentration. Results were compared to the pre-nebulized ones, respectively. Droplet sizes of dispersions nebulized by the two VM devices were assessed by laser diffraction. Therefore, 0.5 ml of a GNP dispersion (1 mg/ml) were nebulized and the vapor was directed through the 633 nm laser beam of a Mastersizer X long bench (Malvern Instruments, Malvern, UK) in 4.5 cm distance to a 300 mm lens. Droplet sizes were calculated by the version 2.19 Mastersizer software using an implemented model based on a particle refractive index of 1.45 and a dispersion optical density of 0.276 at 633 nm. Results are the mean diameter of three runs each with 1000 measuring events. Corresponding FPFs defined as the particle fraction below 5.21 μm were given in percent.

Deposition Study

For deposition studies, fluorescence labeled GNPs with covalently bound Alexa633 dye were employed at a concentration of 1 mg/ml and characterized according to Ph. Eur. by apparatus type A twin-stage glass impinger apparatus (Copley Scientific Ltd., Nottingham, UK,). HPW was introduced in the upper (7 ml) and lower (30 ml) stages of the impinger and a steady flow rate of 60 l/min was maintained during the aerosolization process by a Glax. Sing. Sta. pump (Erweka GmbH, Heussenstamm, Germany) to mimic physiologic breathing air flow. Additionally, a 500 ml aerosol spacer (GSK, Brentford, UK) was introduced as a pre-separator between the VM-nebulizer or pMDI and the impinger. FPF to be found in stage 2 of the impinger was considered the respiratory fraction (RF) as part of the whole nebulized fraction. Results of single fractions were calculated by referring the mass per stage calculated from the detected fluorescence intensity of Alexa 633 labeled GNPs to the whole applied mass of GNPs in the nebulizer and given in percent.

Cell Culture and Immunostimulation

Bronchoalveolar lavage fluid (BALF) was collected from a 20 years old male horse of 520 kg body weight with RAO condition sedated by detomedine (0.01 mg/kg) and butorphanol (0.01 mg/kg) i.v. as previously described. An endoscope was passed nasotracheally for visual inspection of the trachea (Hoffman 2008; Jackson et al. 2004). For local anaesthesia, 10 ml of a 2% mepivacaine solution were passed through the endoscope channel and afterwards the endoscope was pulled back up towards larynx. Subsequently, a BALF catheter (Bivona Inc., Gary, USA) was inserted as far as the bifurcation tracheae, firmly adjusted by a balloon and then employed to introduce two 100 ml aliquots of sterile 0.9% NaCl solution. The 200 ml were immediately aspired again by new sterile syringes and transferred to sterile 50 ml centrifugation tubes. Samples were refrigerated at 4° C. shortly until subsequent centrifugation at 1200 g for 6 minutes to spin down contained cells. The pellet was resuspended in RPMI medium (Biochrom AG, Berlin, Germany) supplemented with 10% FCS and 67.8 μg/ml penicillin and 113 μg/ml streptomycin. Cell numbers were counted using a Neubauer chamber (Laboroptik GmbH, Friedrichsdorf, Germany). 2×105 cells per well were transferred to a 96 well polystyrene cell culture plate (Techno Plastic Products, Trasadingen, Switzerland) and subsequently incubated with either nebulized or non-nebulized 0.275 mg GNPs loaded with 13.5 μg (5% (w/w) CpG. Incubation was set to 24 h at 37° C. in a 5% (V/V) CO2 atmosphere. Afterwards, culture plates were centrifuged at 1200 g for 6 min. and cytokine IL-10 was quantified from collected supernatants by an equine IL-10 ELISA (Duoset, R&D systems, Minneapolis, USA) according to manufacturer's instructions. Detection wavelength was 450 nm. Remaining cell pellets in the well plate were immediately resuspended in 300 μl of 3-(4,5-Dimethylthiazol-2-yl)-2,5-diphenyltetrazolium bromide (MTT) working solution consisting of 82% PBS, 9% FCS and 9% of a 5 mg/ml MTT stock solution. Hence, 0.135 mg MTT reagent was applied per 2×105 cells. After two hours of incubation at 37° C. and in 5% (V/V) CO2 culture plates were centrifuged at 1200 g for 6 min., supernatants were discarded and the remaining pellets resuspended in 200 μl DMSO and subsequently analysed at 590 nm. All samples and related analysis were conducted in triplicate.

Results

Particle Characterization upon Nebulization by pMDI and VM Devices

First, the impact of nebulization by pMDI was assessed. Therefore, vapor fractions were collected, and PCS measurements revealed initial high particle sizes and size distributions (PDI values) that diminished in the course of application. Over a storage time of 48 h, pMDI formulation exhibited no negative impact on unloaded GNPs' stability. As per differential weighing, maximum achieved NE with the pMDI was 77.4% for the 4:1 GNP dispersion:propellant ratio formulation while the others (2:1, 8:1) remained slightly below. After this degree of drawdown, pressure was too low to ensure aerosolization upon liquid's exit from the container via the purging valve. Average dosing was 68 mg formulation per pass. However, the S.D of 20 mg indicated a high variability translating to a relative standard deviation of 29.4%. GNP integrity was indeed not altered over time by the formulation with HFC propellant as most likely no interaction occurred between the hydrophilic GNPs and the inert simultaneously hydrophobic and lipophobic liquid gas (Table 1).

TABLE 1

Particle size and size distribution characterized by the PDI value of GNPs nebulized by pMDI in dependence of the storage time within the pMDI container (n = 3).

| time point [h] | size [nm] | S.D. | PDI | S.D. |
|---|---|---|---|---|
| 0 | 163.8 | 3.8 | 0.173 | 0.036 |
| 1.5 | 150.2 | 1.3 | 0.072 | 0.007 |
| 3 | 152.7 | 1.8 | 0.063 | 0.028 |
| 48 | 153.9 | 2.4 | 0.076 | 0.015 |

For unloaded, fluorescing GNPs with an original size of 145.5 nm (±1.76 nm) and a very low PDI of 0.038 (±0.025), neither VM-nebulization process altered the assessed parameters significantly (Table 2).

TABLE 2

Sizes and size distributions of plain GNPs after nebulization (n = 3).

| c [mg/ml] | size [nm] | S.D. | PDI | S.D. |
|---|---|---|---|---|
| Passive VM device | | | | |
| 0.5 | 149.9 | 1.373 | 0.027 | 0.017 |
| 1.0 | 147.4 | 2.061 | 0.059 | 0.035 |
| 1.5 | 146.2 | 1.601 | 0.024 | 0.015 |
| Active VM device | | | | |
| 0.5 | 144.9 | 1.084 | 0.037 | 0.025 |
| 1.0 | 144.6 | 0.989 | 0.021 | 0.014 |
| 1.5 | 145.6 | 0.734 | 0.032 | 0.023 |

However, CpG-loaded GNPs of another batch being sized 256.2 nm (±3.63 nm) pre-nebulization turned out to be significantly smaller at 222.3 (±1.42 nm) after nebulization by the passive VM device while not being significantly different at 248.2 (±7.34 nm) with the active VM device.

Nebulization Efficiency of VM Devices

NE remained consistent within the repeated measurements for each single device as demonstrated by low S.D. values. Furthermore, the GNP concentration has hardly any impact on the NE. A negligible tendency of higher percentile NE values with rising concentration is visible as it is 93.8, 97.0 and 95.9% and 94.4, 97.0 and 97.8% for the passive VM device and for the glass adapter-supplemented active VM device, respectively. However, the applied VM device has an impact. While the above given values peak near 100%, using the commercial nebulizing body, the active VM device's NE ranks only half at about 50% while the rest is trapped in the device. Recovered masses of re-precipitated samples in the round flak collector were 70.2, 71.7 and 79.1% (m/m), respectively.

Output Rates of VM-Devices

The passive VM-device required a significantly longer period of time to nebulize constantly employed volume of 1 ml of GNP dispersion completely to "dryness" compared to the active VM device (Table 3). Viscosity rose linearly with GNP concentration and accordingly output rates dropped.

TABLE 3

Required nebulization times for three GNP concentrations by two VM devices and related viscosity (n = 3).

| c [mg/ml] | Active VM device | | Passive VM device | | | |
|---|---|---|---|---|---|---|
| | time [min:sec] | S.D. | time [min:sec] | S.D. | viscosity [mPa * s] | S.D. |
| 0.5 | 01:43 | 0.001 | 08:21 | 0.013 | 0.9137 | 0.0003 |
| 1.0 | 01:46 | 0.003 | 08:49 | 0.005 | 0.9201 | 0.0008 |
| 1.5 | 01:53 | 0.002 | 10:57 | 0.024 | 0.9283 | 0.0024 |

With rising GNP concentration, the output rates were only 0.12, 0.11 and 0.09 mg/min, respectively, compared to 4.9 to 5.8 times higher output rates of 0.58, 0.57 and 0.53 ml/min by the active VM device.

Consistency of Concentration after Nebulization

All three employed GNP concentrations were determined gravimetrically before and after nebulization. Post-nebulized concentrations were gained from dispersions precipitated. Results and corresponding deviations of the post-nebulized concentration values to the pre-nebulization values are given in Table 4. Negative deviations indicating lower GNP concentrations are found for all three passive VM device runs. For the active VM device, two deviations were positive indicating a concentration increase and only one was negative. As a trend, deviations got smaller with rising GNP concentration for both VM-devices.

TABLE 4

Comparison of the recovery (absolute and percentile) of three GNP concentrations before and after nebulization by an active and a passive VM device.

| | Active VM device | | | Passive VM device | | |
|---|---|---|---|---|---|---|
| concentration prior nebulization [mg/ml] | concentration after nebulization [mg/ml] | S.D. | deviation through nebulization [%] | concentration after nebulization [mg/ml] | S.D. | deviation through nebulization [%] |
| 0.5 | 0.534 | 0.057 | 6.8 | 0.458 | 0.003 | -8.5 |
| 1 | 0.956 | 0.131 | -4.4 | 0.974 | 0.102 | -2.6 |
| 1.5 | 1.516 | 0.202 | 1.1 | 1.448 | 0.182 | -3.5 |

Aerosol Particle Size Characterization

Analysis of nebulized droplet sizes revealed slightly higher diameters for droplets created by the passive VM device. Here, the mean diameter of the active VM device-generated droplets accounted for 6.60±0.03 µm while those by the passive VM device was determined at 7.46±0.10 µm (±S.D., n=3). Accordingly, the FPF defined below 5.21 µm (Ghazanfari et al. 2007) was 37.13% (±0.57) and 30.24% (±0.97) for the two VM devices, respectively. When nebulizing HPW alone by the Active VM device, a mean droplet sizes of 6.34 µm and a FPF of 36.28% were received.

Deposition Study

Deposition characteristics were assessed impinger-based to estimate each pharmaceutical form's feasibility to deliver GNPs in a high RF to the therapeutically relevant lower airways. GNPs delivered by an pMDI generated aerosol showed a bad deposition related to lower airway targeting as 65.66% (±0.84%) of the nebulized GNP mass were trapped in the spacer and only 0.76% (±5.46%) could be found on the last stage representing the RF (FIG. 1). The passive VM device featured a prospective lung deposition of 47.65% (±18.04%) with 1.95% (±0.91%) ending up in the spacer while the active VM-device exhibited the highest RF value of 65.68% (±11.20%) with 3.43 (±0.40%) to be found pre-separated in the spacer (FIG. 1).

Some particles were deposed on the glass connections and could not be quantitatively assigned to single distinguished stages. They constituted the amount lacking to 100%.

Stimulation of IL-10 Release In Vitro

CpG-ODN loading onto the GNPs' surface was 98.51% (±1.29) according to the gravimetrical differential determination. The Zeta potential was determined to be 23.0 mV (±0.4 mV) before and 21.7 mV (±1.0 mV) after the loading. Conductivity dropped accordingly from 0.943 mS/cm (±0.002) to 0.884 mS/cm (±0.003) due to the reduced amount of chargings present in the dispersion. Once CpGs were successfully loaded onto the GNPs' surface, they were (a) transferred directly without further processing to a cell culture with a defined number of BALF cells or (b) first nebulized by the active VM-device, completely regained from the vapor and added to the cell culture. After 24 h of incubation, ELISAs were performed to determine stimulated cytokine release. Analysis for the central immunomodulating cytokine IL-10 revealed significant higher release for both the nebulized and the non-nebulized formulation compared to the control, untreated BALF cells' supernatant. Difference in release between the two applied GNP groups was not significant and accounted for 225.2 pg/ml (±56.3 pg/ml) and 230.7 pg/ml, respectively (n=3). Additionally, cell viability was very high in both cases, reaching 102.2% (±3.8%) compared to the negative control of amount of untreated viable cells as per MTT assay. Plain, non-loaded GNPs did not trigger IL-10 release in a quantifiable manner and had no negative effect on viability over 24 h.

Example 2

Identification of Eligible Nucleic Acid Active Agents and Proof of Immunomodulating Principle of the Nanoparticulate Composition Oligodeoxynucleotides To evaluate the optimal stimulating CpG motif in cultured equine BAL cells, three different CpG-ODN classes, with previously employed motifs in horses were compared. Five different CpG-ODNs and one ODN without a CpG motif were selected (Biomers GmbH, Ulm, Germany). Each CpG-ODN class was represented by two different sequences, except the A-class where only one sequence was available.

All CpG-ODN classes were single stranded ODNs with a length of 20 to 30 bases. ODN 2041 (5'-CTG GTC TTT CTG GTT TTT TTC TGG-3') was used as a CpG-free sequence. The A class differs in backbone structure from the other classes. It consists of a backbone chimera of phosphorothioate* (PS) and phosphodiester (PD) modified deoxyribose: CpG-ODN A 2216 (5'-G*G*G GGA CGA TCG TCG*G*G*G*G-3'). Two different B-classes were compared: CpG-ODN B 2142 (5'-TCG CGT GCG TTT TGT CGT TTT GAC GTT-3') and CpG-ODN B 2006 (5'-TCG TCG TTT TGT CGT TTT GTC GTT-3'). The C-class was represented by CpG-ODN C 2395: (5'-TCG TCG TTT TCG GCG CGC GCC G-3') and CpG-ODN C M362: (5'-TCG TCG TCG TTC GAA CGA CGT TGA T-3'). A working concentration of 2.5 mg/ml for GNPs and 1.0 mg/ml for ODNs was used. In brief, 76.5 μl of GNP stock solution was diluted by 230 μl highly purified water (HPW) and mixed with 43.8 μl of CpG-ODN stock solution by gentle stirring to obtain a final ODN concentration of 0.125 mg/ml. As references, 0.125 mg/ml CpG-ODN solution of each class (306.5 ml HPW, 43.8 μl CpG-ODN stock solution) and 2.5 mg/ml GNP dispersion (274 μl HPW, 76.5 μl GNP stock solution) were prepared. All the samples were incubated for 90 minutes at room temperature with constant stirring at 300 rpm in a Thermomixer (Eppendorf, Hamburg, Germany). Thereafter, samples were ready for use. The samples were stored at 4° C. and used within 48 hours. Five different CpG-ODN sequences of three different classes and one ODN lacking a CpG motif, as described above, were incubated with the equine BAL cells in triplicate. In detail, 0.275 mg GNPs loaded with 13.5 μg (5% (w/w)) ODN or 13.5 μg of soluble ODN were added per well to compare the effects of unbound ODNs and ODNs bound to GNPs. To estimate the immunostimulating response of ODNs in cell culture, supernatant was taken after 24 hours of incubation and analyzed by equine ELISAs (R&D Systems, Minneapolis, USA). Three key-cytokines namely IL-4, IL-10 and IFN-γ were evaluated. The ELISAs were performed according to the manufacturer's protocol. Limits of detection of the applied ELISA assays were 15.6-2000, 156.25-20000 and 31.2-4000 pg/ml, respectively. Given values were corrected by subtraction of untreated BAL cells, which served as a negative control.

Cell Viability by MTT-Assay

MTT assays were performed to evaluate cell viability following incubation with CpG-ODN and GNP-bound CpG-ODN. After removal of supernatant cell pellets were immediately resuspended in 300 μl MTT (3-(4,5-Dimethylthiazol-2-yl)-2,5-diphenyltetrazolium bromide) working solution consisting of 82% PBS, 9% FCS and 9% of a 5 mg/ml MTT stock solution. Then 0.135 mg MTT reagent was added per $2 \times 10^5$ cells. After two hours of incubation at 37° C. and in 5% (V/V) CO2 the culture plates were centrifuged at 1200 g for 6 min. The supernatant was discarded and the remaining pellets were resuspended in 200 μl DMSO to solubilize violet formazan crystals. The absorbance of each well was measured at 530 nm using wallac Victor$^2$ 1420 multilabel counter (Perkin Elmer, Fremont, Calif., USA). Untreated BAL cells served as a reference for 100% viability. All measured experiments were conducted in triplicate.

Quantification of BAL Cell Subpopulations

To evaluate percentile fraction of BAL cell subpopulations (macrophages, lymphocytes and neutrophile granulocytes) from RAO-affected and healthy horses 1 ml of every BAL cell-pellet was centrifuged two times with 1200 g for 6 min on glass sides. Theses cytospots were stained with diff-quick staining set (Medion diagnostics, Düdingen, Switzerland) and 300 cells respectively were counted manual under microscope. The percentile fraction of macrophages, lymphocytes and neutrophile granulocytes was identified; mean values out of three counts respectively were identified.

Cytokine Release in Cell Culture Upon Stimulation by CpG-ODN/GNP-Bound CpG-ODN

Figure 2:
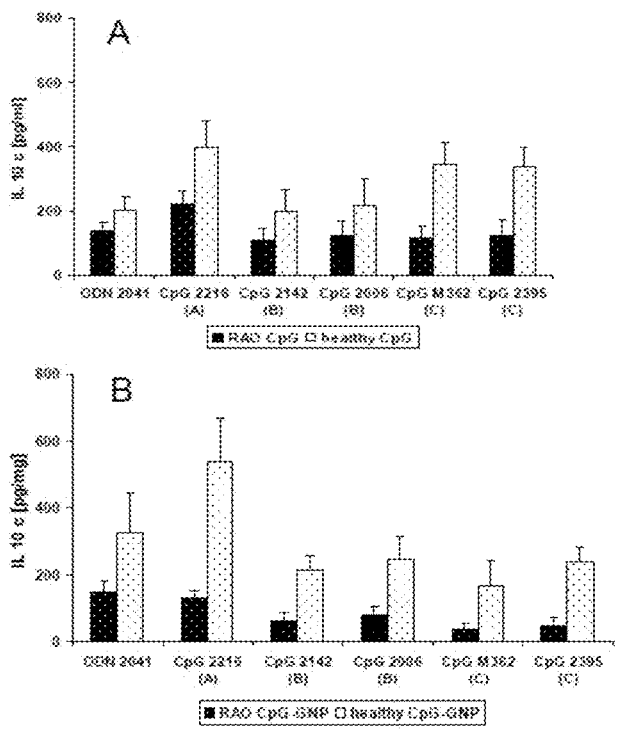

IL-10 Release (Only FIG. 2)

In order to compare the effect of GNP-bound CpG-ODN versus soluble CpG-ODN on cytokine release from BAL cells, six sequences of ODNs (to include five CpG-ODNs) were tested. Throughout, IL-10 showed the highest release in absolute concentration values of the three quantified cytokines. As a general observation, cells from healthy horses secreted significantly (P=0.0047) higher amounts of IL-10 than those of RAO-affected horses. In FIG. 2a IL-10 stimulation of soluble CpG-ODN is shown. Out of the six different ODNs, CpG 2216 (A-class) showed the highest IL-10 release for both examined groups. IL-10 release was 400 pg/ml in cells from healthy horses and 220 pg/ml in those from RAO horses. The B and C class triggered only low levels of IL-10 release in RAO-derived cells, with concentrations of about 125 pg/ml. C-classes appeared to result in higher stimulation (350 pg/ml) than B-class (200 pg/ml) in cell culture from healthy horses. The employed B-classes (ODN 2142 and ODN 2006) and C-classes (ODN M362 and ODN 2395) showed almost identically release behavior in cell culture from RAO horses. In FIG. 2 b IL-10 stimulation by GNP-bound CpG-ODNs is shown. Most noticeable was a significant higher release of IL-10 of the cells from healthy horses (P=0.0051) compared to RAO-affected horses. Furthermore the GNP-bound CpG-ODN 2216 (A-class) induced the highest IL-10 concentration (540 pg/ml) which surpassed the release value by soluble CpG-ODNs as shown in FIG. 2 a. On the contrary the stimulation by other particle-bound CpG-ODNs (B- and C-class) was lower than those by soluble CpG-ODN.

Figure 3:
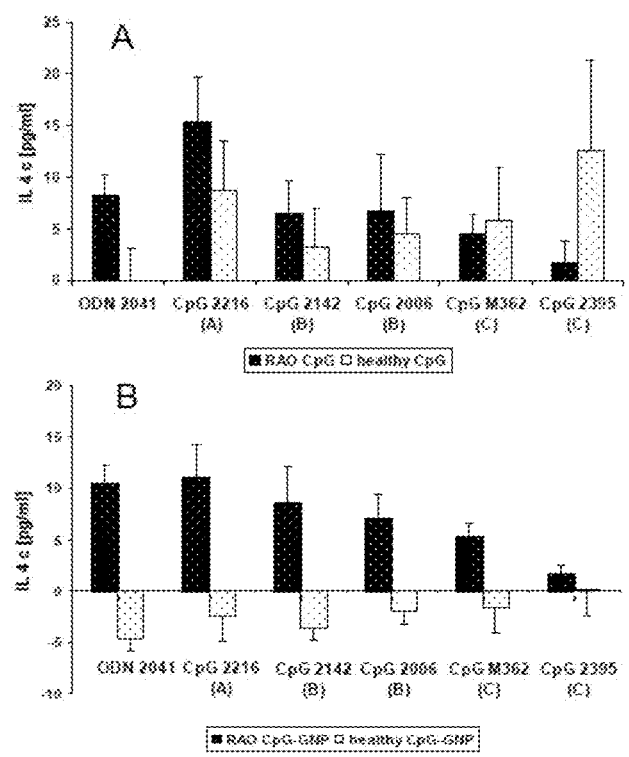

IL-4 Release (only FIG. 3)

In contrast to IL-10, IL-4 release upon stimulation by six soluble ODNs did not differ (P=0.614) between RAO and healthy horses derived cells (FIG. 3 a). Both absolute values were low and inter and intra variations were high. However, as shown in FIG. 3 b, difference of high significance (P=0.001) was found when comparing GNP-bound CpG-ODN stimulated cell cultured from RAO and healthy horses for IL-4 release. The latter resulted in negative values (FIG. 3 b) while those of RAO-affected horses were positive and not distinguishable from those provoked by soluble CpG-ODN (P=0.9469). Furthermore GNP-bound CpG-ODN lowered IL-4 release of cells of healthy horses considerably more than soluble CpG-ODN (P=0.0018) (FIG. 3 a).

IFN-γ Release

IFN-γ release from RAO and healthy horses derived cell cultures is displayed after stimulation by soluble CpG-ODNs. On average, no significant difference could be observed between the mean values of cells from RAO-affected and healthy horses (P=0.3514). However, the six employed ODNs revealed distinctive effects. As seen for IL-10, the highest release was induced by CpG 2216 A-class and accounted for 94±10 pg/ml in RAO and 135±19 pg/ml in healthy horses derived cell cultures. All other ODNs induced lower amounts between 15 and 50 pg/ml. A tendency towards higher release by healthy horse derived cells could be assumed but was not statistically significant. In contrast, GNP-bound ODNs led to a clear discrimination between RAO and healthy derived cells in terms of IFN-γ (P=0.008). Here, CpG 2216 A-class stimulated the highest IFN-γ secretion as well, accounting for 76±14 pg/ml (healthy) and 25±10 pg/ml (RAO). In this individual example (CpG 2216), a marginally statistically not significant difference was found (P=0.05). Also, no or slight release from RAO cell cultures was found, while no statistical significance occurred between the healthy derived cell cultures treated by CpG-ODN in comparison with GNP-bound CpG-ODN (P=0.45).

MTT Assay

BAL cells from RAO-affected and healthy horses were used to investigate in vitro cell viability after 24 h of incubation with regard to detectable differences after administration of soluble CpG-ODNs compared to GNP-bound CpG-ODNs. Four mean values (cells from RAO horses on the one hand treated with CpG-ODN or with GNP-bound CpG-ODN and cells from healthy horses on the other hand treated with CpG-ODN or GNP-bound CpG-ODN), were averaged out of the individual viability results of the six employed ODNs. Untreated BAL cells were assessed as 100% viability reference. In the healthy group no significant differences were detectable in viability between soluble CpG-ODN and GNP-bound CpG-ODN administration. No significant differences were seen between the six ODNs examined individually. Of all evaluated means of the four groups, lowest viability was observed in cells from RAO-affected horses treated with soluble CpG-ODN (69.7%±6.6%). In comparison, cells from RAO-affected horses with GNP-bound CpG-ODN showed the highest viability, on average 104.3%±6.4%, which was significantly higher (P<0.0001). As an example, difference between cells treated with CpG-ODN 2216 A-class and cells treated with GNP-bound CpG-ODN 2216 A-class was found to be significant (P=0.0405). However, mean viability of cells from healthy horses exposed to soluble CpG-ODN was 94.2%±4.0% and with GNP-bound CpG-ODN administration 91.7%±8.0%. No significant differences were observed between these two mean values (P=0.512). Accordingly, no significant difference was identified in the CpG-ODN 2216 A-class example (P=0.5319). Cells derived from RAO-affected and healthy horses did not differ in viability when challenged GNP bound CpG-ODN 2216 A-class (P=0.808). Summarizing, BAL cells gained from RAO-affected horses showed significant higher cell viability in MTT assay when incubated with GNP-bound CpG-ODN in comparison to soluble CpG-ODN. This difference was not seen in assays with cells gained from healthy horses.

With regard to the results, the optimal stimulating sequence among five explored CpG-ODNs in equine BAL cells was the A-class 2216. The detectable IL-10 upregulation was higher than expected as CpG-ODNs were previously known for potent IFN-γ release in general and CpG-ODN A-class for IFN-α release in particular (Krieg, 2002). With regard to the observation that no significant difference of IL-10 release within B- and C-class by cells from RAO-affected horse was detectable, we could hypothesize that the class is more determining than the individual CpG-ODN sequence.

Example 3

Preliminary Clinical Study as Proof of Principle in a Therapeutic Clinical Setting Nebulization of the Immunomodulating Nanoparticulate Composition For inhalation studies, an Equine Haler™ spacer (Equine HealthCare Aps, Hoersholm, Denmark) and an active VM device were combined by a 90° glass connector with ground joints that suitably matched the aerosol generator part's outlet diameter and the spacer's inlet. An identical protocol was run for negative control placebo trial and for the medication trial. The negative control exclusively contained an aqueous (HPW) GNP dispersion (1.5 mg/ml) while the medication was a combination of GNP (1.5 mg/ml) and CpG-ODN 2216 (0.075 mg/ml). Healthy and RAO-affected horses were inhaled three times alike with two-day intervals between individual administrations followed by a control BAL. Two additional subsequent inhalations and one final BALF examination for disease development monitoring were added if significant changes occurred after the third inhalation. Clinical examinations, blood gas analysis, endoscopic exploration and cytology of TBS were performed at the beginning, after three and finally after five inhalations.

Clinical Examination and Lung Scoring

A lung scoring system was further developed comprising clinical parameters (nasal discharge, breathing rate), blood gas chemistry, endoscopic exploration, cytology of tracheobronchial secret (TBS) and of bronchoalveolar lavage fluid (BALF). Accordingly, 12 horses of a mean weight of 477.7 kg and aged 12.0 years on average were scored. The study was approved by the regional legal agency for animal experiments (Regierung von Oberbayern, Munich, Germany) and designated the approval code 55.2-1-54-2531-31-10. The applied scoring system allowed grouping the patients into four categories (healthy, mild, moderate and severe RAO). For the clinical trial, three groups of horses were established, with the first group (n=4) consisting of healthy horses (mean age of 8.8 years) for the placebo negative control, the second group (n=4) consisting of healthy horses for compatibility study (mean age of 10.4 years) and the third group (n=4) of moderate RAO-affected horses for therapeutic efficiency verification (mean age of 16.8 years). The key arterial blood gas parameter of partial pressure of oxygen ($PaO_2$) was measured by a Radiometer Copenhagen NPT 7 series (Radiometer GmbH, Willich-Schiefbahn, Germany). Physiological values for $PaO_2$ were set to 100 mmHg (±5 mmHg). Moreover, percentages of neutrophil granulocytes out of total cell count from TBS cytology were calculated after staining by Diff-Quick® staining set (Medion diagnostics, Diidingen, Switzerland). Physiological range of breathing rate was defined as 8 to 16 breaths per minute while higher values were considered as pathological.

Figure 5:
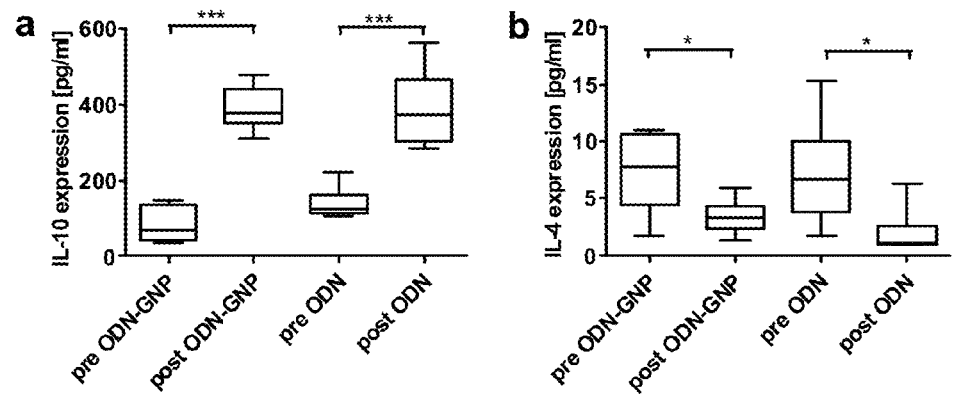
Figure 6:
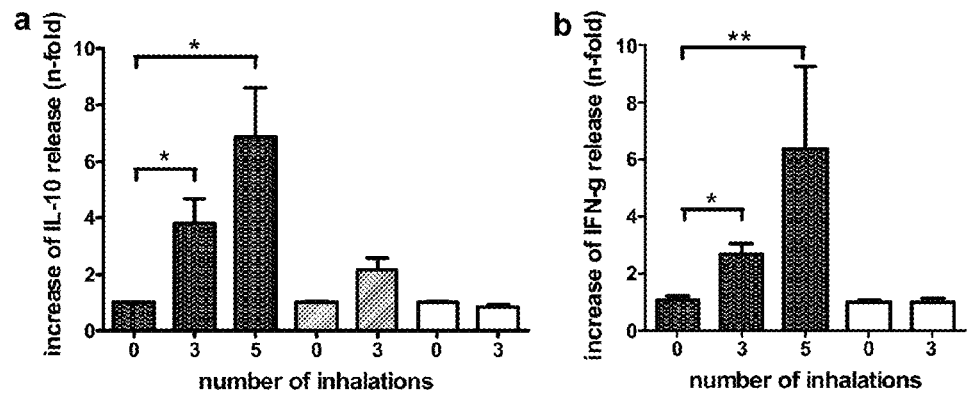
Figure 7:
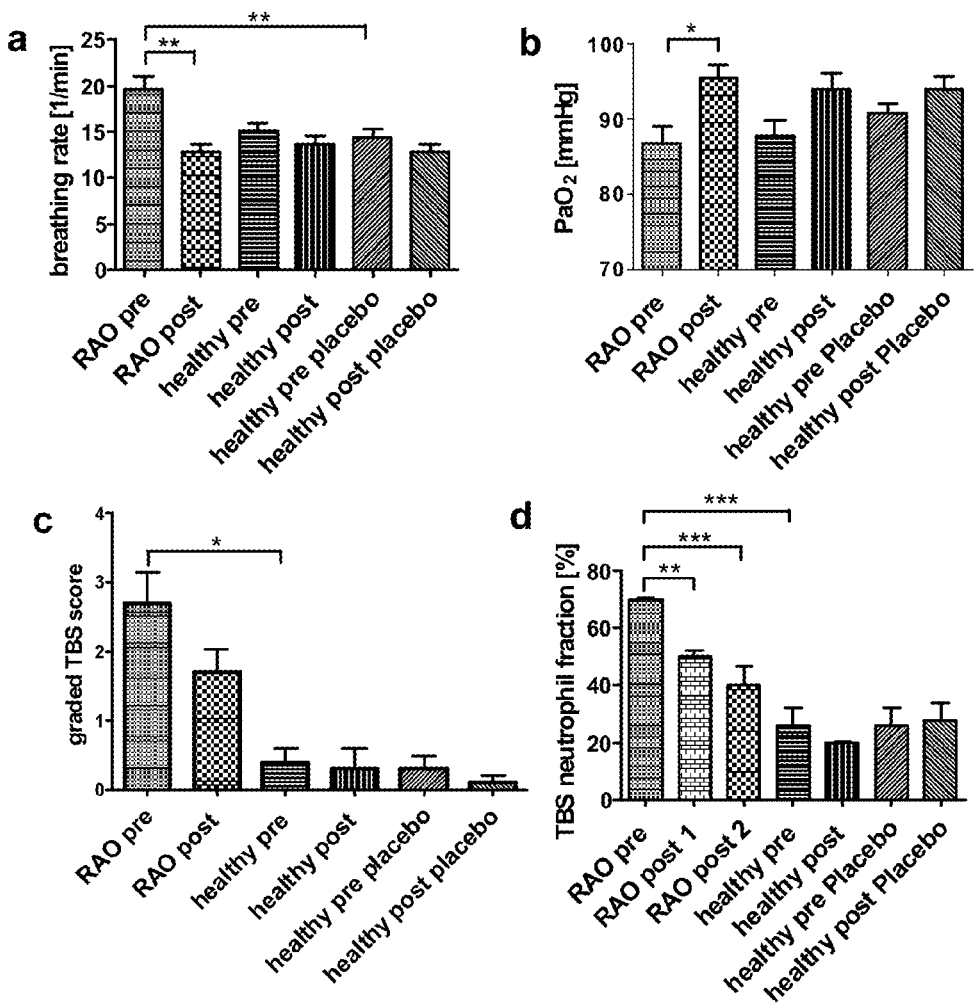

Results (Only FIGS. 5 to 7)

To evaluate the efficiency of envisaged inhalation therapy, BALF was obtained before and after the regimen from RAO-affected and healthy horses. Data from healthy individuals served as physiological reference. BALF cells were stimulated in vitro by six different ODNs. In FIG. 5a shows in vitro IL-10 expression of cells derived from RAO-affected horses treated by ODNs and GNP-bound ODNs both before and after inhalation. After inhalation treatment, a significantly (P<0.0001) higher IL-10 release (390 pg/ml) in BAL cell cultures stimulated by GNP-bound ODNs was observed as compared to the state before inhalation treatment (83 pg/ml) (FIG. 5a). Similar trend of IL-10 release was observed after stimulation (389 pg/ml) by soluble ODNs (FIG. 5a) compared to the value of 139 pg/ml before inhalation regime (P=0.0002). Accordingly, IL-4 in vitro expression was decreased significantly after inhalations of both soluble (P=0.0298) and GNP-bound (P=0.0282) ODNs (FIG. 5b).

Overall, IFN-γ release in vitro was low and did not reveal a general trend after treatment by GNP-bound ODNs (P=0.1414) or by soluble ODNs (P=0.4870) before (pre)

versus after (post) inhalation treatment of RAO-affected horses. FIG. 6a clearly depicts the increase of IL-10 expression detected in BALF supernatant in RAO-affected horses. While three inhalations led to a significant 3.8-fold increase (P=0.0473) in IL-10 expression, a 6.9-fold increase was found after five inhalations (FIG. 6a). Therefore, the average IL-10 levels differ significantly (P=0.034) before starting and after finishing the full five inhalation regimen applied to RAO-affected horses. Healthy horses exhibited a 2.14 fold augmentation in IL-10 expression after pulmonary administration of GNP-bound CpG-ODN confirming the principle of action (FIG. 6a). However, differences in expression levels before and after inhalation were marginally statistically significant (P=0.089). In contrast, no significant difference (P=0.289) was found when comparing healthy horses before and after three pulmonary administrations of blank GNPs which was given as placebos (FIG. 6a). In vivo secretion of IL-4 and IFN-γ was analyzed in BALF supernatants before and after inhalation regimens. IL-4 levels were below detection threshold in vivo. For IFN-γ, a significant impact of GNP-bound CpG-ODN regimen was observed. FIG. 6b reveals a constant increase after three and five consecutive inhalations compared to IFN-γ levels in BAL supernatants before the regimen (P=0.0034). Placebo administration did not result in altered cytokine expression (P=0.8322) (FIG. 6b) while IFN-γ data could not be obtained from healthy individuals treated with GNP-bound CpG-ODN.

Firstly, the breathing rate per minute was assessed to discriminate healthy and RAO-affected individuals. The latter exhibited a breathing rate of 19.6 (±1.47) breaths per minute (bpm) before treatment (FIG. 7a) which was significantly higher than the measured value 13.6 (±0.98) bpm of healthy horses (P=0.0094). The regimen (five doses) lowered the rate significantly down to 12.8 (±0.80) bpm (P=0.0036) (FIG. 7a).

Healthy horses had a $PaO_2$ of 94 mmHg (±2.07) (FIG. 7b). In contrast, RAO-affected horses showed a $PaO_2$ of 86.75 mmHg (±2.29) (FIG. 7b). This mean value was significantly improved (P=0.0153) towards 95.6 mmHg (±1.69) by the full regimen of five inhalations (FIG. 7b). Thereafter, no statistically significant difference was observed compared with the healthy animals (P=0.5384). The percentage of neutrophil granulocytes within the TBS of RAO-affected horses was high (70%±0.50) before treatment and differed significantly from values of healthy horses exhibiting 26% (±6.0) (P=0.0004) (FIG. 7d). Treatment by GNP-bound CpG-ODN contributed to a significant decrease down to 50% (±2.04) by three inhalations (P<0.0001) and down to 40% (±6.52) by five inhalations (P=0.0048), respectively (FIG. 7d). After fife applications of GNP-bound CpG-ODN no statistically significant difference could be observed compared to healthy horses (P=0.195). Furthermore, FIG. 7d shows that in healthy horses neither the GNP-bound CpG-ODN (P=0.3472) nor the placebo (P=0.8171) resulted in a significant change of neutrophil percentages, respectively.

Beside cytokine-based immunologic parameters, the clinical impact of the hereby proposed therapy was assessed. No local or systemic adverse effects after inhalation of GNP-bound CpG-ODN (CpG-GNP) were observed indicating the good biocompatibility of applied doses and regime. This is the first time an in vivo application of nanoparticle-bound immunostimulating DNA via inhalation in horses is reported in this study.

The inhalation regimen lowered the breathing rate of RAO-affected horses significantly and can therefore be regarded efficient.

The determination of partial pressure of blood oxygen ($PaO_2$) was used to evaluate the extent of gas exchange and the response to treatment. The magnitude of gas exchange abnormality correlates with the severity of bronchiolitis and clinical signs.

Within TBS, the percentage of neutrophil granulocytes represents a strong indicator for RAO. Moreover, it is regarded as one of the most decisive parameters to evaluate RAO. As a consequence an average decrease of 40% of neutrophils in TBS cytology after fife inhalations with GNP-bound CpG-ODN could be estimated as one of the most important clinical ameliorations after this immunotherapy. The percentage of neutrophils within the TBS was directly related to the severity of the RAO condition. Therefore, it can be deducted that the severity of the pathogenesis was significantly reduced after five applications of GNP-bound CpG-ODN Previously, $T_{reg}$ activation was related to a reduction in activity and the number of neutrophile granulocytes by promoting their rate of apoptosis. Human neutrophils express all known TLRs except TLR3. Moreover, TLRs were shown to possess a crucial impact on $T_{reg}$ stimulation and function. Previous investigations confirmed that $T_{reg}$ cells inhibit neutrophils other than by direct cell-cell contact mechanism (CTLA-4/B7-1 mechanism) and especially through IL-10 action. Furthermore, this mechanism was advantageous in the treatment of allergic diseases. Therefore, it is concluded that the observed impressive IL-10 induction by the hereby proposed treatment can be directly related to the decreasing neutrophils' percentage and therefore directly contributes to the regimen's anti-RAO effectiveness. Consequently, further studies with higher patient numbers and dose escalation are in preparation in order to elucidate the full potential of this first applied inhalative nanoparticle based immunotherapy.

Example 4

Evaluating the Long Term Effect of the Present Composition on Symptoms of Allergic and/or Inflammatory Diseases of the Lower Airways Method
24 horses suffering from an allergic and inflammatory disease affecting the lower airways, i.e. RAO, enrolled in a placebo-controlled clinical study evaluating the long-term efficiency of the immunomodulating nanoparticulate composition of the present invention. The individuals were examined for decisive parameters associated with the allergic and inflammatory disease affecting the lower airways prior the treatment cycle with comprised 5 inhalations each separated by a treatment-free day. Clinical examination was further performed 1d and 28 d after the last administration. The immunomodulating nanoparticulate composition was administered by VM-facilitated nebulization via a combined spacer as depicted in FIG. 4.
Results and Discussion
Decisive clinical parameters such as partial oxygen blood pressure and breathing frequency neared physiologic values, i.e. they were significantly increased and decreased in contrast to placebo treatment, respectively. Further clinical parameters such as trachea mucus quantity and viscosity, coughing, nasal discharge, bifocatio and percentage of neutrophils in the tracheal mucus could be significantly lowered, leading to tremendous improvement for the quality of life of the affected individuals. Importantly, the observed improvements were found significant even after 28 d from the last administration indicating a long-lasting therapeutic effect.

The invention claimed is:

1. A method for the treatment of an allergic or inflammatory disease of the lower airways in a mammal, comprising administering to the mammal a therapeutic effective amount of a pharmaceutical composition via inhalation, comprising a pharmaceutically acceptable polymerized protein-based nanocarrier and as active agent a guanidine phosphodiester cytosine (CpG) oligodeoxynucleotide (ODN), wherein the CpG ODN is a class A CpG ODN, wherein the polymerized protein-based nanocarrier is a gelatin nanoparticle, an albumin nanoparticle, a legumin nanoparticle, a gliadin nanoparticle, a beta-galactoglobuline nanoparticle or a silk protein nanoparticle, and wherein the class A CpG ODN is bound to the surface of the polymerized protein-based nanocarrier reversibly via electrostatic interaction, and wherein the method has a therapeutic effect in the treatment of an allergic or inflammatory disease of the lower airways of at least 4 weeks.

2. The method according to claim 1, wherein the pharmaceutical composition is a dry powder or a nebulized aqueous dispersion or a nebulized aqueous dispersion made from a lyophilisate.

3. The method according to claim 2, wherein the nebulized aqueous dispersion is nebulized by a vibrating mesh nebulization device, wherein the resulting droplet size in the nebulized aqueous dispersion is in the size range between 1 to 5 μm, wherein the respirable droplet fraction is 50 to 100%, wherein the nebulization efficiency is more than 95%, wherein the nanoparticle concentration within the aqueous dispersion is in the range between 1.0 to 2.0 mg/ml, wherein a dispersant in the aqueous dispersion is highly purified water with a conductivity below 0.55 μS/cm or a physiological 0.9% NaCl solution, wherein the aqueous dispersion has a viscosity in the range between 0.85 and 1.1 mPa/s, and wherein the nebulized aqueous dispersion is nebulized by a vibrating mesh nebulization device at an output rate over 0.5 ml/Min.

4. The method according to claim 1, wherein the ODN is administered at a low, side-effects-avoiding dose of 0.0001 to 2 mg per kg body weight or in a range between 0.0001 and 0.01 mg/kg body weight or in a range between 0.0002 and 0.001 mg/kg body weight.

5. The method according to claim 1, wherein the CpG ODN comprises a central palindrome CG motif-containing sequence flanked by a polyG sequence and a chimerical phosphodiester/phosphorothioate backbone.

6. The method according to claim 1, wherein the CpG ODN is selected from the group consisting of SEQ ID NO:2, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and a derivative of each sequence, wherein the derivative comprises a chimerical phosphodiester/phosphorothioate backbone or a full phosphorothioate backbone.

7. The method according to claim 1, wherein the CpG ODN induces the release of immunomodulating cytokine interleukin-10.

8. The method according to claim 1, wherein the mammal is a human, horse, dog, cat, cow, pig, sheep, goat, mouse, rat, elephant, giraffe, or hippopotamus.

9. The method according to claim 1, wherein the amount of CpG ODN is 0.1 to 10 wt % or 1 to 7.5 wt % or 5 wt % in relation to the nanoparticle mass.

10. The method according to claim 1, wherein the pharmaceutical composition further comprises an excipient selected from the group consisting of buffer salts, surfactants, lyoprotectors, dyes, chelating agents and radionuclides.

11. The method according to claim 1, wherein the administration is via inhalation, wherein a vibrating mesh nebulization device is combined with an inhalation spacer in such a manner that the mammal can inhale the nebulized pharmaceutical composition from the inhalation spacer, and wherein the vibrating mesh nebulization device is attached to the inhalation spacer, so that the nebulized pharmaceutical composition is quantitatively available to the individual at the inhalation spacer's top part nasal outlet.

12. The method of claim 1, wherein the pharmaceutical composition is administered 1 time per day, 2 times per day, 3 times per day, 4 times per day, 5 times per day, 6 times per day, 1 time per week, 2 times per week, 3 times per week, 4 times per week, 5 times per week or 6 times per week, 3 times per months, 2 times per months or 1 time per month.

13. The method of claim 1, wherein the pharmaceutical composition is administered in a cycle comprising a period of 3 to 14 d with 3 to 7 applications followed by an application-free period of 7 to 84 d.

14. The method according to claim 1, wherein the composition further comprises an additional antiantiallergic or anti-inflammatory active agent selected from the group consisting of glucocorticoids, H1-antagonists, leukotriene antagonists, mast cell stabilizers beta2-adrenergic receptor agonists, and anticholinergic agents.

15. The method of claim 1, wherein the pharmaceutical composition is prepared by contacting the nanocarrier with the sole active agent in a ratio of 90 to 99% nanocarrier to 1 to 9% active agent in a pharmaceutically acceptable medium, sensitive mixing and incubating for 0.5 to 6 h at a shaking rate of 200 to 800 rounds per minute, purifying and adjusting the concentration so that the composition can be nebulized.

* * * * *